United States Patent [19]
Phillips et al.

[11] Patent Number: 5,522,393
[45] Date of Patent: Jun. 4, 1996

[54] MULTI-DIMENSIONAL REAL-TIME ULTRASONIC BLOOD FLOW IMAGING APPARATUS AND METHOD

[75] Inventors: Patrick J. Phillips, Durham; Olaf T. von Ramm, Efland, both of N.C.

[73] Assignee: Duke University, Durham, N.C.

[21] Appl. No.: 248,342

[22] Filed: May 24, 1994

[51] Int. Cl.$^6$ .................. A61B 8/06; G01F 1/66
[52] U.S. Cl. .................... 128/661.09; 73/861.25
[58] Field of Search .............. 128/660.05, 660.07, 128/661.01, 661.08–661.10; 73/625–626, 861.25; 364/413.25

[56] References Cited

U.S. PATENT DOCUMENTS

| | | | |
|---|---|---|---|
| 4,550,607 | 11/1985 | Maslak et al. | 73/626 |
| 4,878,500 | 11/1989 | Ophir et al. | 128/660.01 |
| 4,937,797 | 6/1990 | Snyder et al. | 128/661.01 |
| 4,972,838 | 11/1990 | Yamazaki | 128/661.09 |
| 4,984,188 | 1/1991 | Kato | 364/725 |
| 5,231,573 | 7/1993 | Takamizawa | 128/661.08 X |
| 5,261,408 | 11/1993 | Maslak et al. | 128/661.01 |
| 5,355,888 | 10/1994 | Kendall | 128/660.07 |
| 5,357,964 | 10/1994 | Spivey et al. | 128/661.09 |
| 5,363,849 | 11/1994 | Suorsa et al. | 128/661.08 |
| 5,398,216 | 3/1995 | Hall et al. | 128/661.08 X |
| 5,421,333 | 6/1995 | Takamizawa et al. | 128/661.01 |
| 5,441,052 | 8/1995 | Miyajima et al. | 128/661.09 |

Primary Examiner—Francis Jaworski
Attorney, Agent, or Firm—Richard E. Jenkins

[57] ABSTRACT

An ultrasonic diagnostic apparatus and method for real-time multi-dimensional blood flow imaging with enhanced sensitivity to lateral blood flow. The apparatus constitutes an improvement on the ultrasonic diagnostic apparatus of the type wherein an ultrasonic pulse beam is repeatedly transmitted into the subject under examination at a fixed pulse rate and the reflected echoes are picked up, amplified and displayed. The improvement comprises an ultrasonic transducer means comprising a phased array transducer which is electronically and/or mechanically divided into two or more independently controlled sub-apertures and adapted for transmitting ultrasonic pulse beams from one of the two or more sub-apertures and for receiving the reflected echoes with at least two of the two or more sub-apertures. Optionally, the apparatus and method further comprises signal processing means including quadrature detection circuitry comprising sampling means for sampling the echo signals or a downward shifted version of echo signals and Hilbert transform means for filtering the signals so as to obviate the need for mixers, low-pass filters (LPF) and quadrature reference frequencies utilized in conventional ultrasonic blood flow imaging.

30 Claims, 19 Drawing Sheets

KEY:
TX = TRANSMIT GROUP
RX₁, RX₂ = RECEIVE GROUP

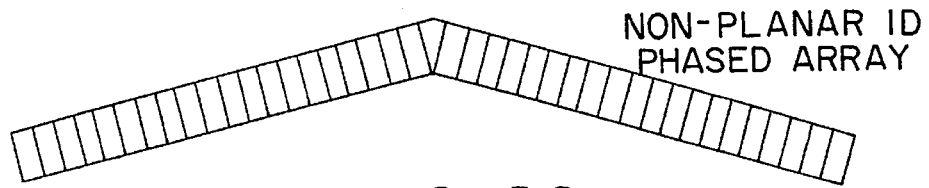
FIG. 20a  NON-PLANAR 1D PHASED ARRAY
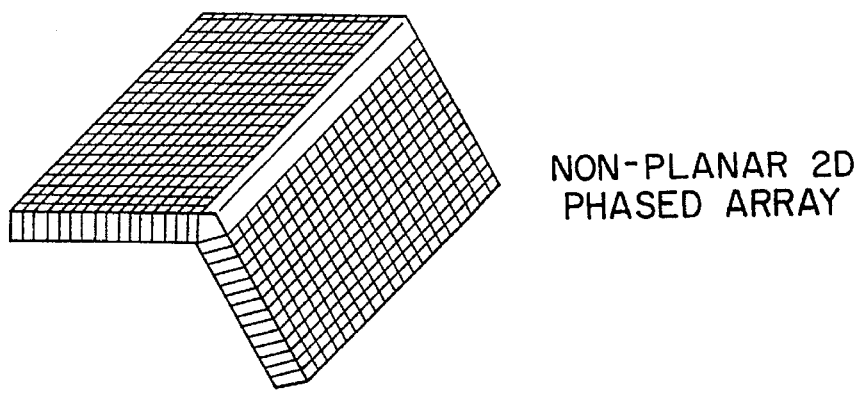
FIG. 20b  NON-PLANAR 2D PHASED ARRAY
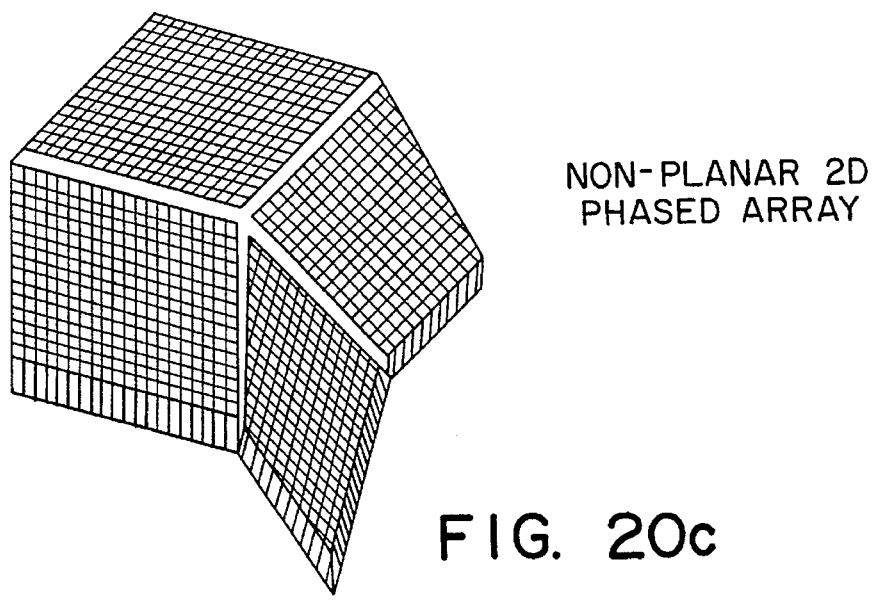
FIG. 20c  NON-PLANAR 2D PHASED ARRAY
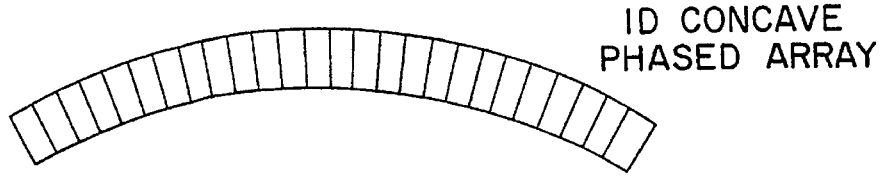
FIG. 20d  1D CONCAVE PHASED ARRAY

MULTI-DIMENSIONAL REAL-TIME ULTRASONIC BLOOD FLOW IMAGING APPARATUS AND METHOD

GOVERNMENT INTEREST

This invention was made with Government support under Grant CA-37586 and CDR-8622201 awarded by the National Institute of Health (NIH) and National Science Foundation (NSF), respectively. The Government has certain rights therein.

TECHNICAL FIELD

The present invention relates to an ultrasonic blood flow imaging apparatus for multi-dimensional real-time acquisition of blood flow information within a patient under examination and display of the blood flow information as a multi-dimensional image.

DESCRIPTION OF THE BACKGROUND ART

Diagnostic medical ultrasound scanners have become indispensable tools for clinicians because they can provide blood-velocity information in real time. Spectral Doppler (blood-velocity spectra displayed as a function of time) provides quantitative information from a single range-gated area that is vital in such areas as vascular disease, cardiac function and fetal health, while color flow mapping (superposition of color coded mean velocities and variances on a grey-scale anatomical image) compliments this and is more commonly used for qualitative analysis of blood flow.

While the routine use of these tools is rapidly increasing, they can detect and display only a one-dimensional projection (onto the axis of the ultrasound beam) of the natural three-dimensional blood flow velocities. In spectral Doppler, this projection is calculated using an angle correction that can be estimated by using the surrounding anatomy, such as the orientation of vessel walls, as a guide. However, this manual correction is rarely accurate or repeatable and flow may not necessarily be parallel to vessel walls. In color flow mapping, mean velocities are calculated with no angle correction, resulting in an angle dependency that may vary across the image. This dependency is influenced both by the scanning geometry of the transducer and the anatomy that is being scanned (e.g., curvature of vessels). The angle dependency of current systems and the chosen display methodologies often produce inhomogeneous images that are not good representations of the actual flow field. More recently, many of the ultrasonic imaging apparatus manufacturers have introduced a new feature in their machines called "power-mode Doppler", which acts to color code the estimates of the instantaneous power rather than instantaneous mean frequency, of the received Doppler signal. While this offers an improvement in sensitivity and eliminates some of the inhomogeneities of normal color flow mapping, vital velocity and directional information is rejected in the process.

To overcome these limitations, scanners must detect and display more than a one-dimensional projection of the three-dimensional blood flow velocity vectors. Prototypes have shown that this can be done but none has been introduced commercially or used on a routine clinical basis due to a number of common limitations. These limitations independent or in combination are among the following:

(1) limited fields of view: many attempts have only found success using a single point or range gate within a B-mode image;

(2) Impractical transducer assemblies: often these assemblies consisted of more than one transducer fixed into a large impractical handle that was not useful in the clinical environment;

(3) Too few piezoelectric elements and many attempts did not utilize a phased array transducer but rather a few single-element piston transducers;

(4) Alignment problems: mis-aligned interrogating beams were not from the same point in space; (5) Reduced frame-rates: real-time operation was not possible with the method chosen; and (6) Non-simultaneous interrogations from more than one angle: for example—techniques that relied on ECG triggering to acquire multiple interrogations lost the attraction of being real-time and were often susceptible to inaccuracies due to acceleration of the blood flow in between interrogations.

One embodiment of the novel apparatus of the invention measures the magnitude and direction of blood flow velocity vectors over an adequate two-dimensional field of view at frame rates equivalent to those presently available in commercial scanners. The technique uses conventional phased array transducers or more specialized phased array transducers and demands only a modest increase in processing power. Following the theoretical description hereinbelow, applicants present an error analysis based on a set of simulations which demonstrate the apparatus' ability in conveying unambiguous and accurate velocity estimates. Then applicants present results from experimental work which used a blood-mimicking phantom, further demonstrating the feasibility of the invention for the case of measuring two-dimensional velocity vectors. This is followed by a discussion of results and a practical description of the invention including a description of the optional novel quadrature circuitry used in the practice of the invention.

DISCLOSURE OF THE INVENTION

Conventional ultrasonic blood flow imaging utilizes ultrasonic transducer means adapted to repeatedly transmit ultrasonic pulse beams into a subject under examination and to receive reflected echoes of the ultrasonic pulse beams from within the subject and convert the reflected echoes into echo signals. Signal processing means convert the reflected echo signals via Doppler signal processing into image signals, and display means serve to visually output the image signals as an image. Applicant's improvement to conventional ultrasonic blood flow imaging apparatus comprises utilizing an ultrasonic transducer means comprising a phased array transducer which is electronically and/or mechanically divided into two or more independently controlled sub-apertures and adapted for transmitting ultrasonic pulse beams from one of the two or more sub-apertures and for receiving the reflected echoes with at least two of the two or more sub-apertures. In this fashion, real-time multi-dimensional blood flow imaging with enhanced sensitivity to lateral blood flow is achieved by the apparatus of the present invention.

Also, applicant contemplates an improved method for ultrasonic blood flow imaging wherein conventional ultrasonic blood flow imaging methodology is utilized but improved upon by electronically and/or mechanically dividing the phased array transducer (e.g., the ultrasonic transducer means) into two or more independently controlled sub-apertures and transmitting ultrasonic pulse beams from one of the two or more sub-apertures and receiving the reflected echoes with at least two of the two or more sub-apertures. In this fashion, real-time multi-dimensional blood flow imaging with enhanced sensitivity to lateral blood flow is achieved.

Optionally, both the novel apparatus and method described hereinabove contemplate the use of quadrature detection circuitry within the signal processing means for sampling the RF (radio frequency) echo signals or a downward shifted version of the echo signals, and filtering the samples of the signals with Hilbert transformations. The use of the novel quadrature detection circuitry obviates the necessity for mixers, low pass filters (LPF), quadrature reference frequencies, and complexity associated with matching analog channels required by conventional ultrasonic blood flow imaging apparatus circuitry.

It is therefore the object of the present invention to provide an improved apparatus and method for diagnostic ultrasonic blood flow imaging.

It is still another object of the present invention to provide an improved ultrasonic imaging apparatus and method for multi-dimensional real-time ultrasonic blood flow imaging.

It is still another object of the present invention to provide an improved ultrasonic imaging apparatus and method to obtain greater imaging sensitivity and accuracy to lateral blood flow in real-time imaging.

Some of the objects of the invention having been stated, other objects will become evident as the description proceeds, when taken in connection with the accompanying drawings described in detail below.

BRIEF DESCRIPTION OF THE DRAWINGS

FIGS. 20A–20D is a schematic drawing showing a non-planar, one-dimensional (1D) phased array configuration utilizing two sub-apertures; a non-planar, two-dimensional (2D) phased array configuration utilizing two two-dimensional sub-apertures; a non-planar, two-dimensional (2D) phased array configuration utilizing four two-dimensional sub-apertures; and a non-planar, one-dimensional (1D) phased array configuration utilizing a concave configuration, respectively.

BEST MODE FOR CARRYING OUT THE INVENTION

Theortical Description of the Invention

Figure 1:
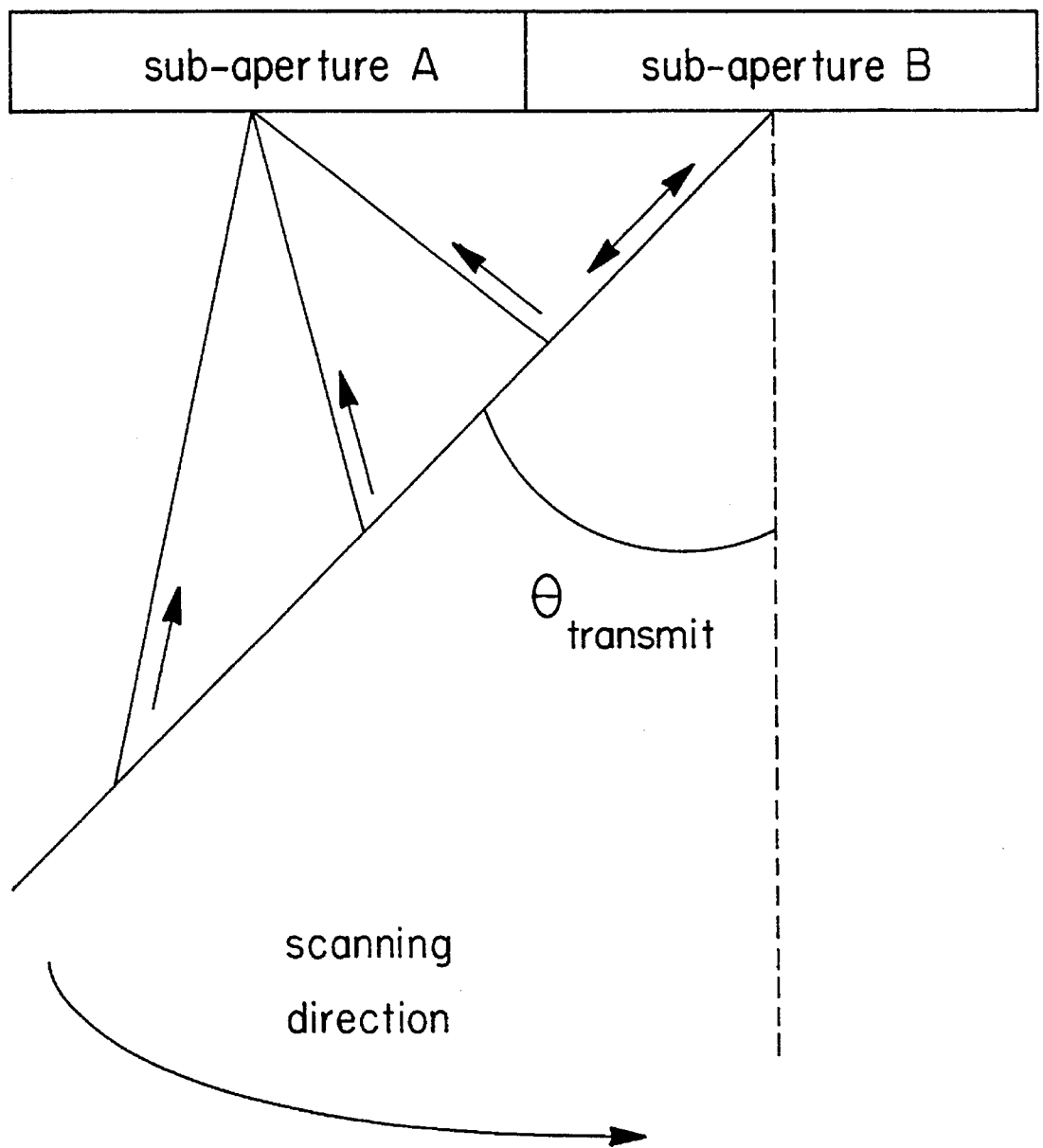
FIG. 1 shows a scanning configuration with a phased-array transducer wherein sub-aperture B scans in a conventional back-scattered phased-array format, while sub-aperture A receives angular-scattered echoes by tracking the transmitted beam formed by sub-aperture B.

Most suitably, a conventional phased array transducer of an ultrasonic blood flow imaging apparatus is electronically subdivided into two sub-apertures which are spatially separated from each other. A beamformer is used to steer and focus the ultrasound simultaneously and independently from each sub-aperture. A conventional ultrasound pulse is transmitted from one of the sub-apertures and then both sub-apertures are simultaneously used for reception. A possible two-beam scanning configuration is shown in FIG. 1. Note that the receiver for sub-aperture A must track echoes along the direction of the acoustic burst transmitted from sub-aperture B. The specifics of an angular-scattering image system are well known. With this angular-scatter, beam-tracking technique, the sub-aperture size and location could be altered dynamically throughout the scanned plane.

After both of the independent sub-apertures receive the reflected pulses, the returned signals are processed simultaneously for motion or flow information in the conventional way. Alternatively, the signals from each sub-aperture could be processed separately if the signals were stored, though the frame rate would be reduced by a factor of two. Once complete, this processing yields spectral Doppler information and mean frequency estimates from two different and known directions. From these, an estimate of the two-dimensional velocity, magnitude and direction in the plane of the scan can be computed. In the experiments described herein, applicants use the well known autocorrelation estimator described by Namekawa et al.; Omoto et al.; Miyatake et al.; and van Leeuwen et al. for computing the mean frequency and estimates.

Using the well-known Doppler equation:

$$|\bar{v}|\cos\theta = \frac{c\bar{f}}{2f_0} \quad (1)$$

where:

$|\bar{v}|$=magnitude of velocity $\theta$=angle between ultrasound beam and flow vector direction c=speed of sound in the medium $\bar{f}$=instantaneous frequency of the Doppler signal $f_0$=center frequency of transmitted pulse and relating it to the known transducer geometry (FIG. 2), it is then possible to calculate the magnitude of the flow vector $|\bar{v}|$ and its direction $\theta_v$ relative to the coordinate system indicated with the beamforming reference to transmit sub-aperture for this one possible realization.

For the back-scatter case applicants measure the frequency $\bar{f}_B$ using sub-aperture B where:

$$\bar{f}_B = \frac{2|\bar{v}|\cos(\theta_B)f_0}{c} = \frac{2|\bar{v}|\cos(\theta_v - \theta_t)f_0}{c} \quad (2)$$

while for the angular-scatter case applicants measure the frequency $\bar{f}_A$ using sub-aperture A where:

$$\bar{f}_A = \frac{|\bar{v}|[\cos(\theta_A) + \cos(\theta_B)]f_0}{c} = \quad (3)$$

-continued
$$\frac{|\bar{v}|[\cos(\theta_v - \theta_r) + \cos(\theta_v - \theta_t)]f_0}{c}$$

Solving for the magnitude and the angle of the flow velocity yields:

$$|\bar{v}| = \frac{\bar{f}_B c}{2f_0 \cos(\theta_v - \theta_t)} \quad (4)$$

$$\theta_v = \tan^{-1}\left\{\frac{2\left(\frac{\bar{f}_A}{\bar{f}_B}\right) - 1 - \cos\theta_{beams}}{\sin\theta_{beams}}\right\} + \theta_t \quad (5)$$

where:

$$\theta_{beams} = \sin^{-1}\left[\frac{S\cos(\theta_t)}{(R^2 + S^2 + 2RS\sin(\theta_t))^{1/2}}\right] \quad (6)$$

The cases to consider when solving for the above quantities are:

1. If both $\bar{f}_A$ and $\bar{f}_B$ are non-zero, then equations (4) and (5) apply.
2. If $\bar{f}_B$ is zero, then the direction of flow is perpendicular to the beam formed by sub-aperture B and hence the angle $\theta_v$ is equal to $90°+\theta_t$; $|\bar{v}|$ is calculated using equation (3).
3. If $\bar{f}_A$ is zero, then the direction of flow is perpendicular to the line bisecting the sector formed by the beams from the two sub-apertures, hence, the angle $\theta_v$ is equal to $90°+\theta_t+(\theta\text{beams}/2)$; $|\bar{v}|$ is found using equation (4).
4. If both $\bar{f}_A$ and $\bar{f}_B$ are zero, then the flow is assumed to be zero and no calculation is necessary. In practice, transmit time effects and noise will produce individual frequency estimates that may have significant statistical variance. To reduce this variance and to increase the accuracy of the computed velocity vector field, it will be necessary to introduce a thresholding scheme in the system. This thresholding scheme could consist of a type of averaging of individual frequency estimates, computed vectors, spacially computed frequency estimates or vectors, or a combination of these.

Based upon preliminary estimates the above calculations could be performed in real time with a mid-range digital signal processor or easily performed with simple dedicated hardware. The frequencies from each sub-aperture could be calculated in parallel with no loss in frame time.

Error Analysis

A series of simulations were undertaken by applicants to characterize errors in the calculated quantities as functions of errors in the measured quantities. The question addressed was how errors in the mean frequency estimates affect the calculated 2-D velocity magnitude and direction over a chosen field of view. Applicants found that the best way to present the results of these simulations was a series of simulated color B-scans of a uniform flow field, as these illustrate the resulting 2-D spatial homogeneity of the technique.

Figure 2:
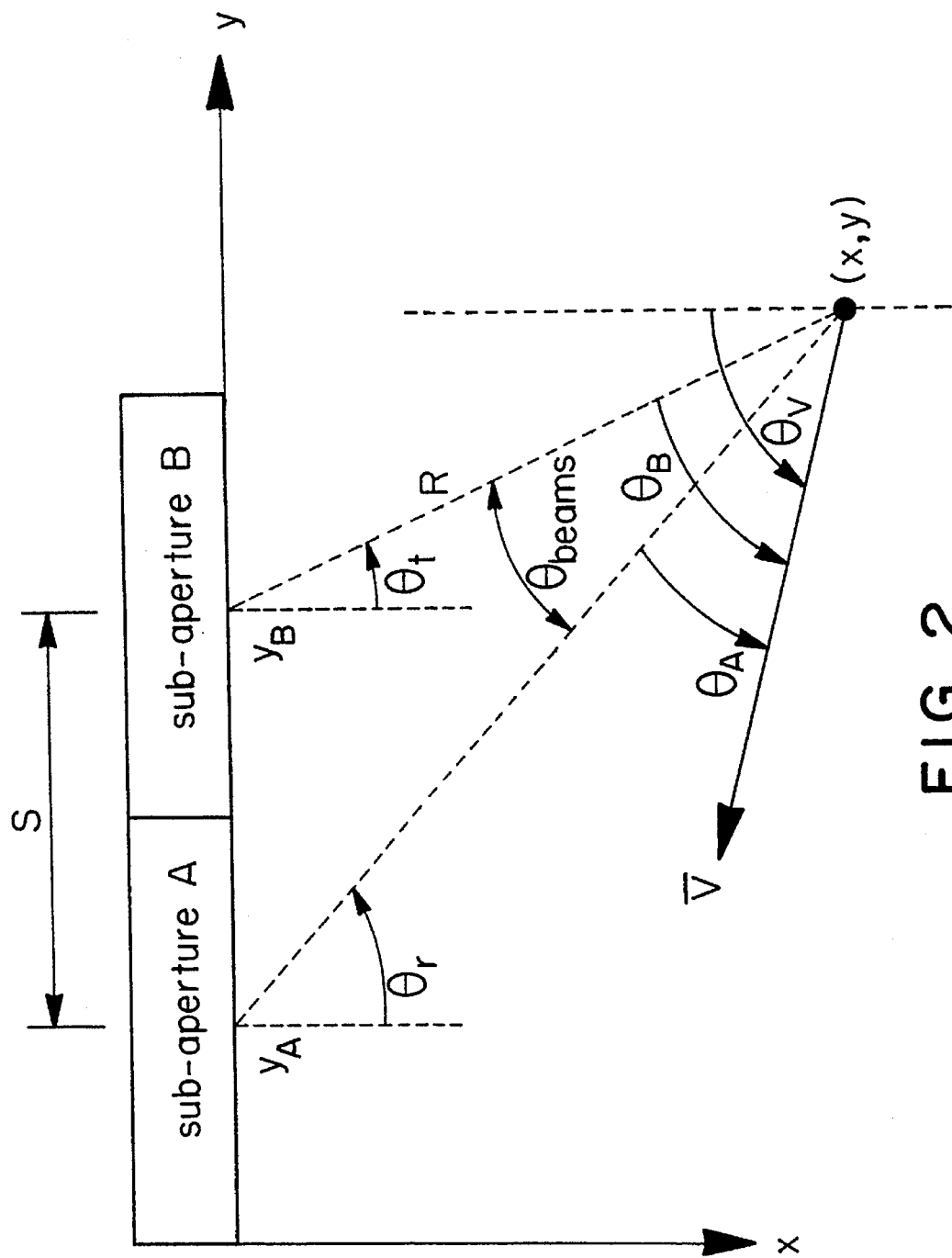
FIG. 2 shows an array geometry adopted for multiple-beam reception.

A 40 mm phased-array transducer with a center of 2.0 MHz was simulated with its face along the y-axis equally divided into 2 sub-apertures, as shown in FIG. 2 ($^YA$=10 mm, $^YB$=30 mm). A phased-array scan format was used with a maximum depth of 100 mm and a width of 40 mm. After assigning an arbitrary flow-velocity magnitude and direction for each scan, the mean frequency was calculated for each sub-aperture. To model a realistic imaging environment, perturbations of a fixed percentage about the mean values, as well as a random component, were introduced into mean frequency estimates. The fixed error component models systematic errors, such as bias in the mean frequency estimates due to frequency-dependent attenuation, frequency-dependent scattering ,and clutter filtering, while the variable random component models noise.

Figure 3:
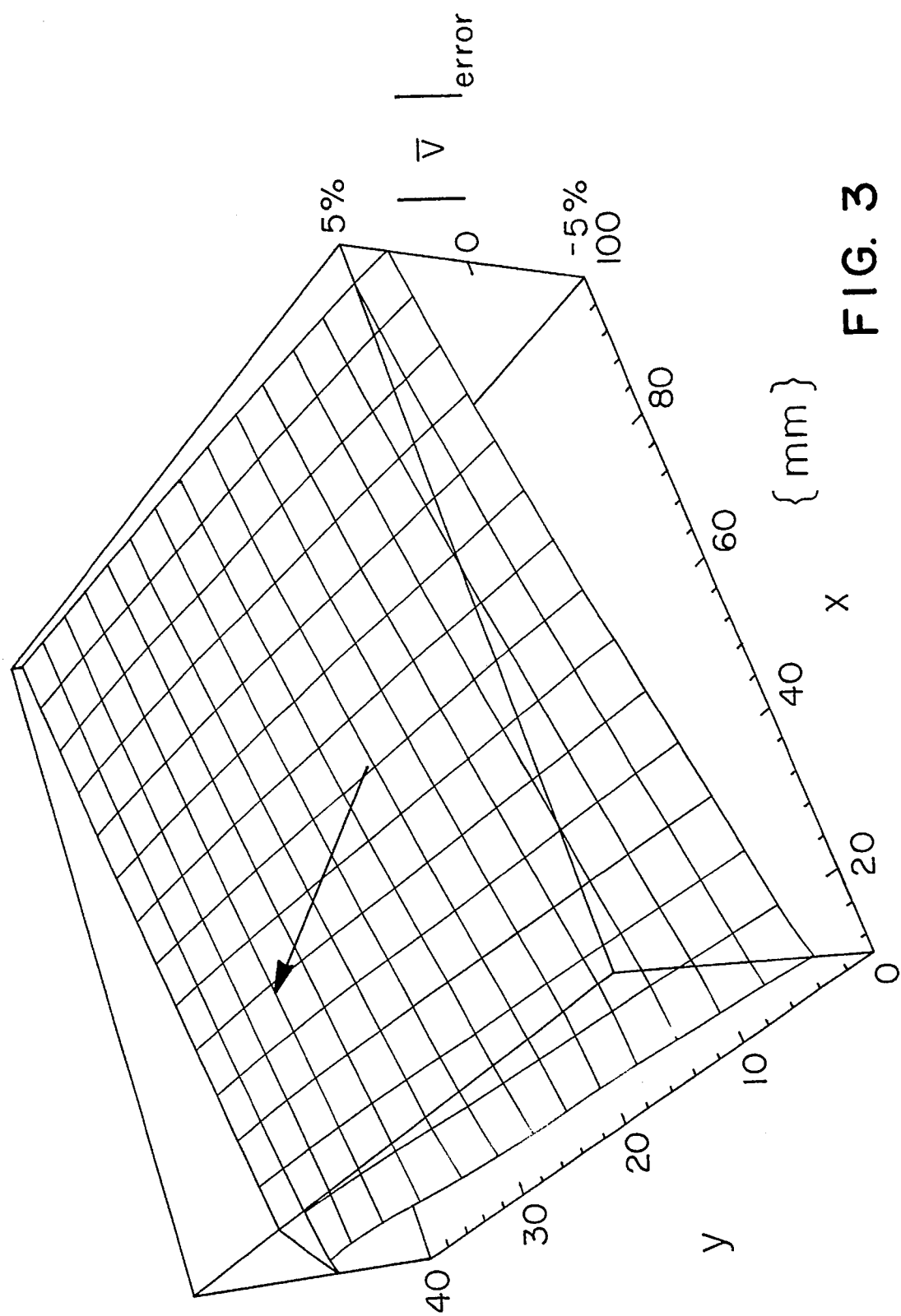
FIG. 3 shows a plot of error in estimated local velocity magnitude as a function of position in the scanning plane wherein the transducer face is simulated along the y-axis and a 1% systematic error in the mean frequency value for sub-aperture B was introduced.
Figure 4:
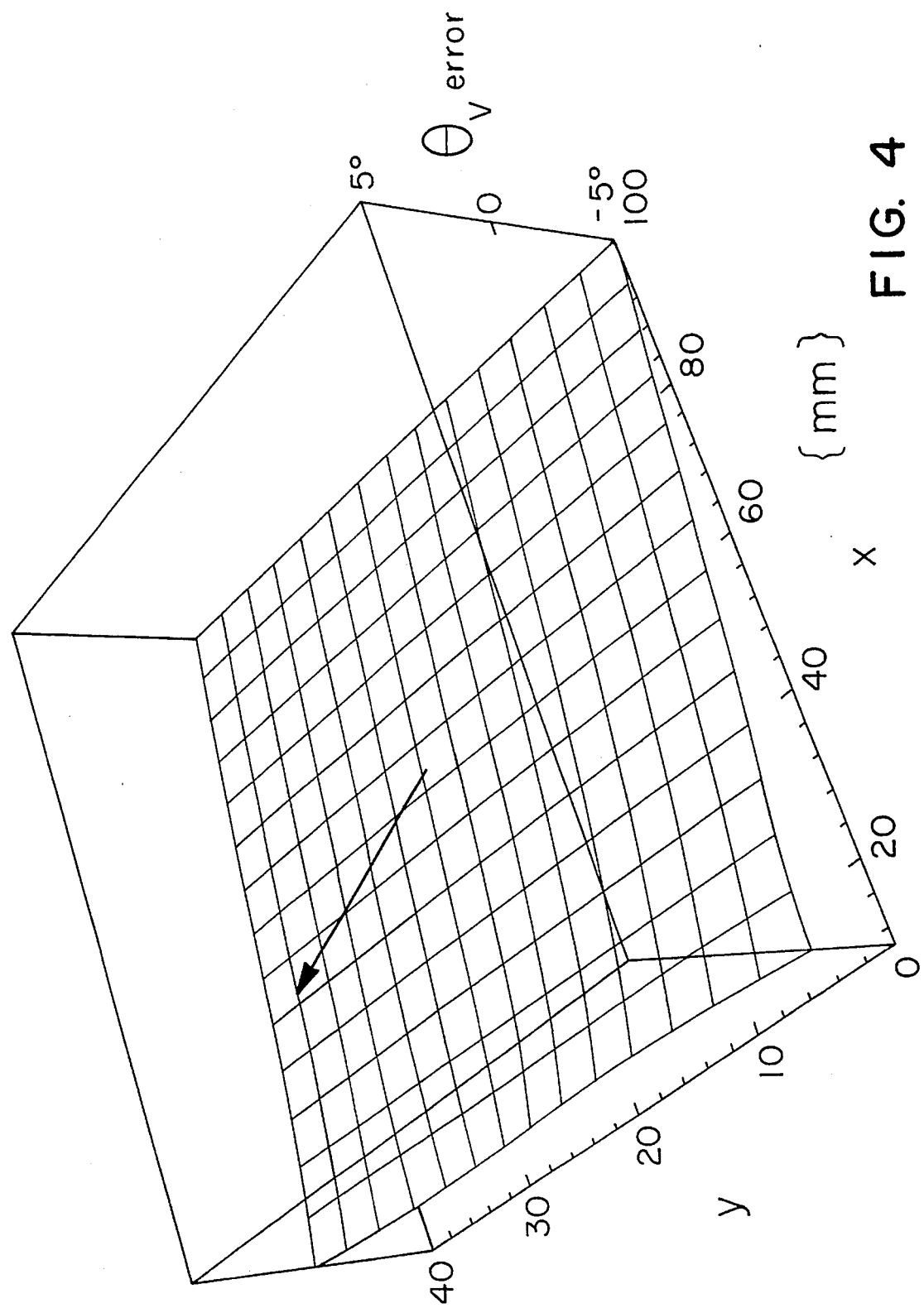
FIG. 4 shows a plot of error in the estimated local velocity direction as a function of position in the scanning plane under the same conditions as FIG. 3.

The results are shown in FIGS. 3 through 10. FIG. 3 shows the perturbation in the displayed 2-D velocity magnitude as a function of the field position (x,y). Here, there was a systematic error of 1% in the mean frequency value for sub-aperture B, no error in sub-aperture A, no random errors, and flow was at 45° with respect to the transducer face (indicated by the arrow). FIG. 4 shows the perturbation in the calculated flow angle under the same conditions. These graphs show that there is a slowly varying inhomogeneity in the calculated flow field. Additional simulations confirmed that the orientation of the 2-D error surface as shown in these graphs depended upon the flow direction, but the magnitude of the largest error was independent of the flow direction.

Figure 5:
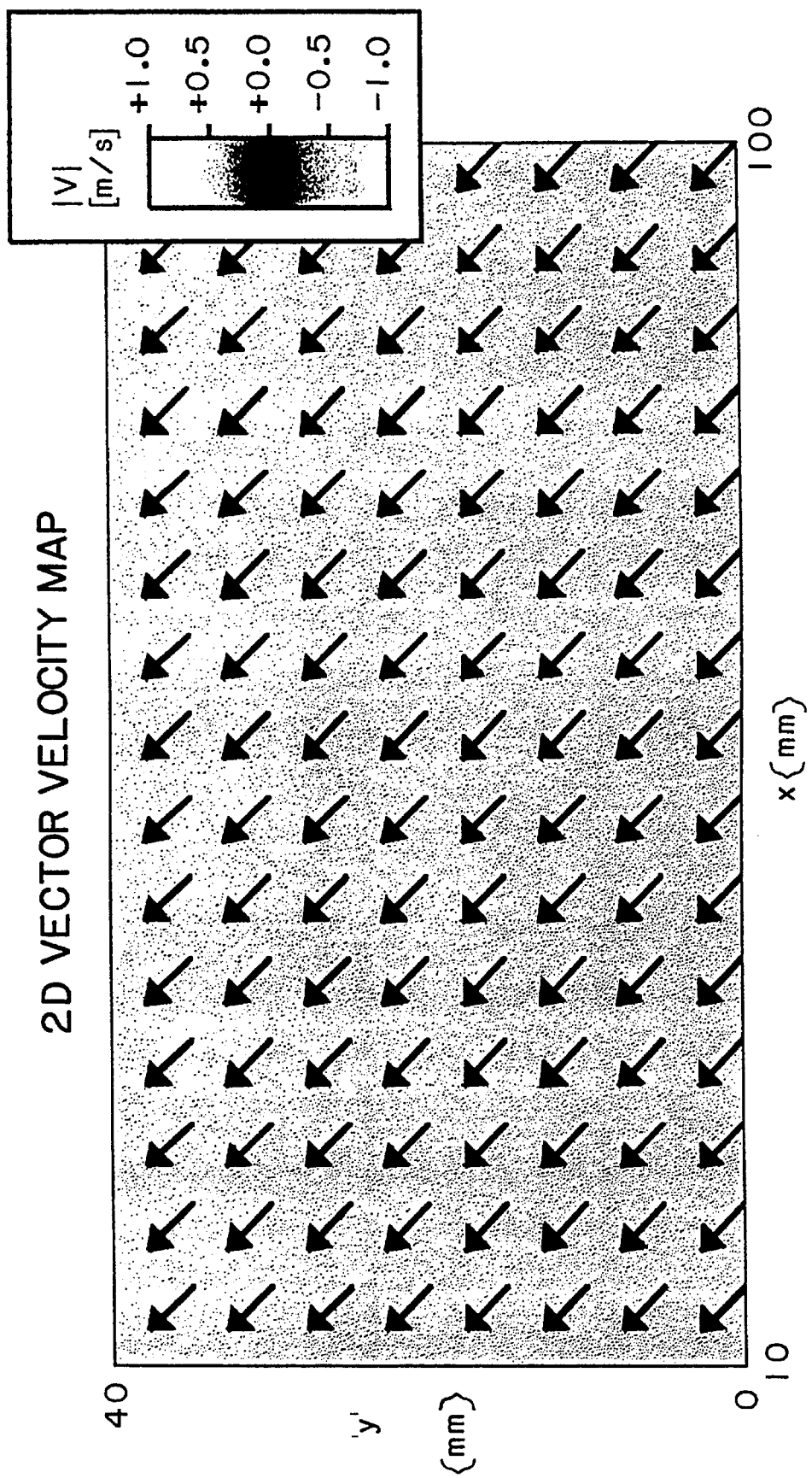
FIG. 5 shows a simulated two-dimensional vector velocity map of a uniform flow field of 0.5 ms$^{-1}$ at 45° relative to the transducer face wherein no errors were introduced and the center frequency of the array was 2.0 MHz and wherein the vectors indicate local velocity magnitude and direction while the color indicates velocity magnitude (the transducer face along the y-axis).
Figure 6:
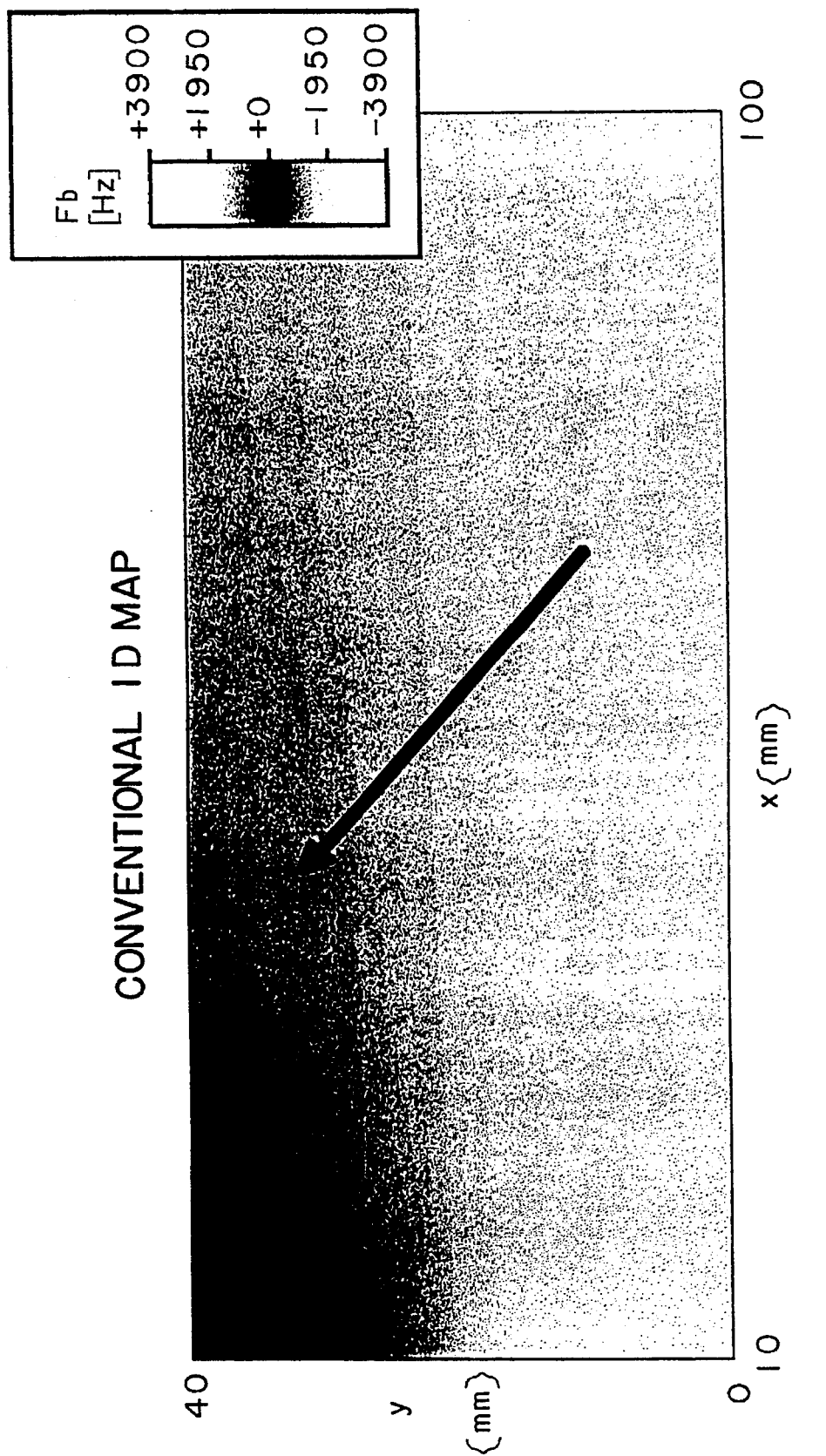
FIG. 6 shows a simulated conventional one-dimensional color flow map of the same flow field as in FIG. 5 wherein no errors were introduced and wherein the face of a linear array transducer, with a center frequency of 2.0 MHz, was placed along the y-axis and its entire aperture used to produce the scan.
Figure 7:
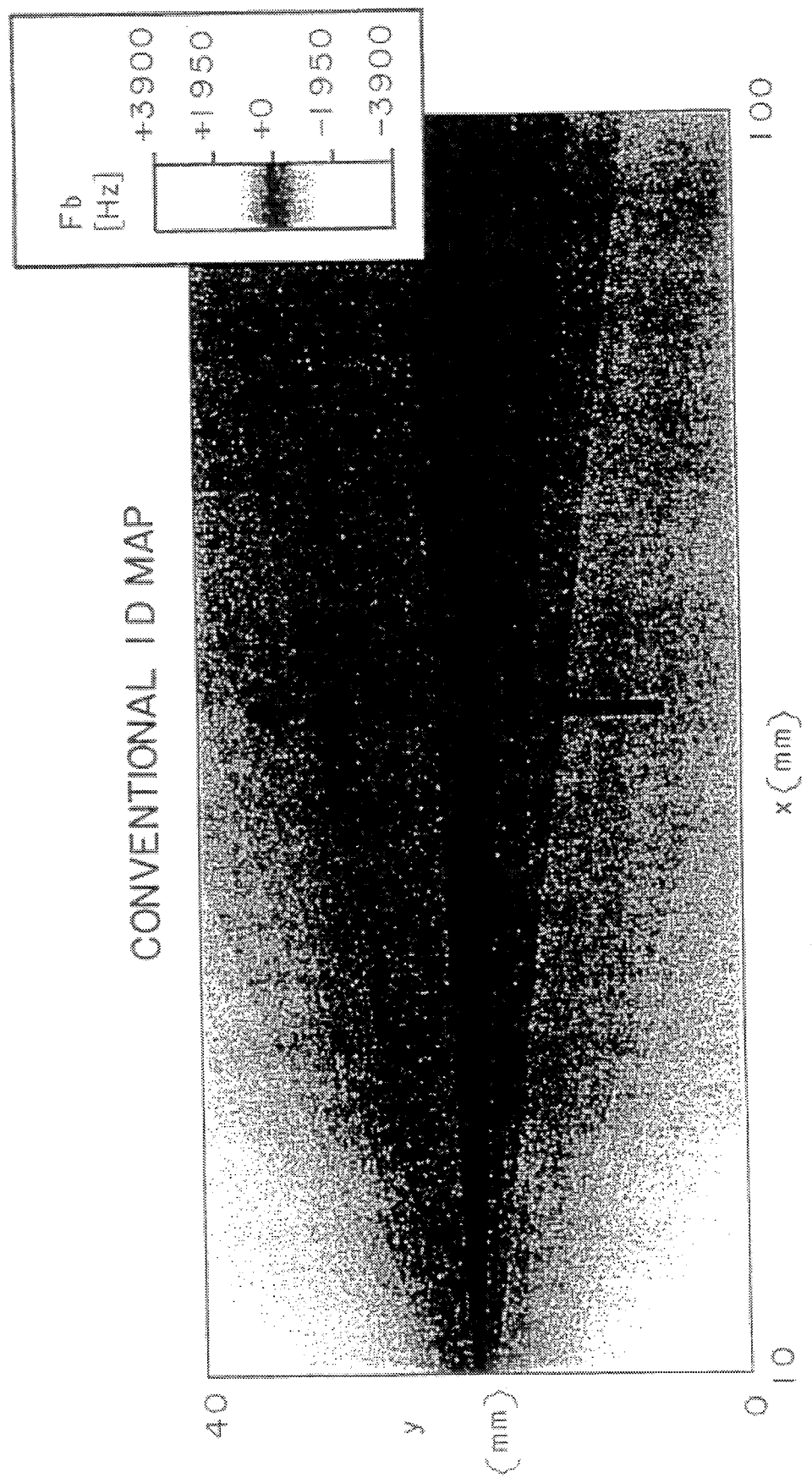
FIG. 7 shows a simulated conventional one-dimensional color flow map of a uniform flow field at 0.5 ms$^{-1}$ at 90° (parallel) to the face of the transducer (indicated by arrow) wherein no errors were introduced and the transducer face is along the y-axis.

To simulate how this inhomogeneity might appear in a real system implementation, applicants used color to represent the magnitude of velocity and small arrows to depict both the magnitude and direction of the localized flow. FIGS. 5 through 7 show ideal simulated scans of uniform flow fields using a conventional color map. Here, red changing to yellow indicates increasing velocity magnitude towards the transducer face (as used in conventional 1-D systems) and dark blue changing to light blue indicates increasing velocity magnitude away from the transducer face. FIG. 5 shows an ideal 2-D velocity map with flow at 45° to the transducer face while FIGS. 6 and 7 show conventional 1-D velocity maps (using the entire array aperture) with flow at 45° to 90° to the transducer face respectively. Due to the angle dependency of these conventional systems significant inhomogeneities exist in the displayed field.

Figure 8:
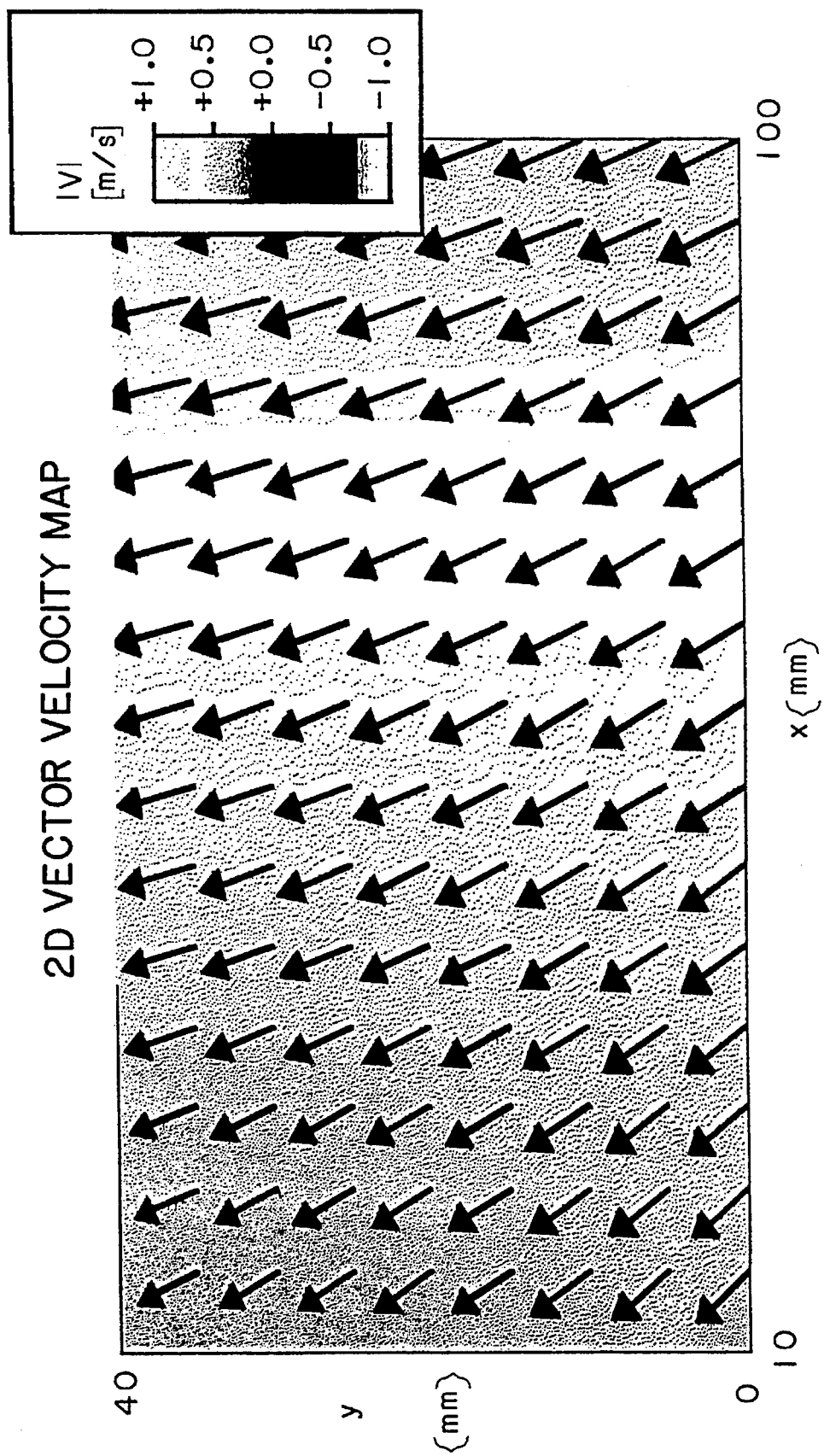
FIG. 8 shows a simulated two-dimensional vector velocity map of a uniform flow field (shown in FIG. 5) with a systematic error of −20% in the mean frequency estimate from the back-scatter sub-aperture (upper half of array) and a systematic error of −10% in the estimate from the angular-scatter sub-aperture (lower half of array).
Figure 9:
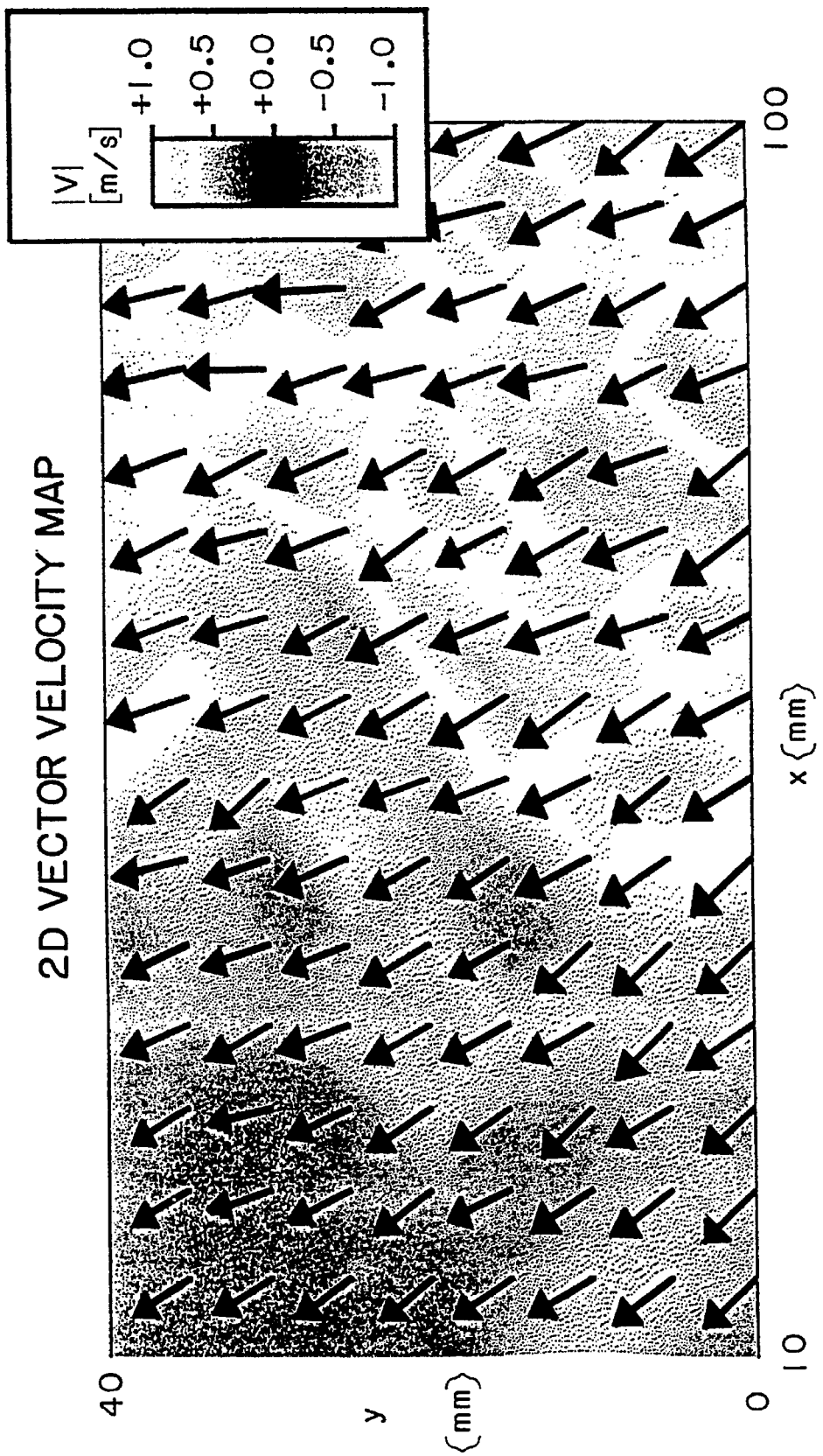
FIG. 9 shows a simulated two-dimensional vector velocity map of a uniform flow field (shown in FIG. 5) with systematic errors identical to those in FIG. 8 but with an additional spatially random error of ±5%.
Figure 10:
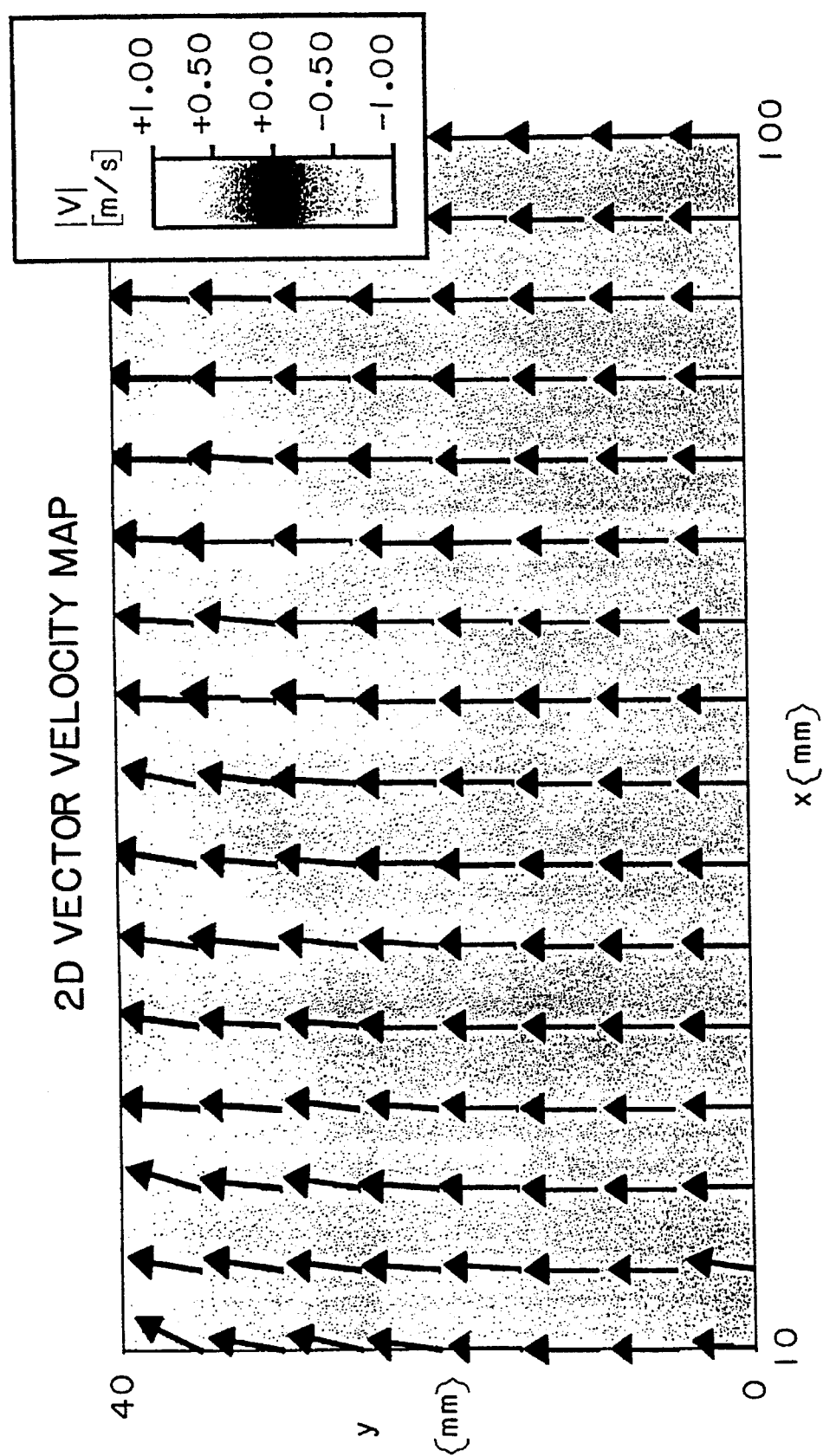
FIG. 10 shows a simulated two-dimensional vector velocity map of a uniform flow field at 90° with the same introduced error conditions as in FIG. 9.

FIGS. 8 through 10 show results for applicants' 2-D mapping technique with the introduction of errors. FIG. 8 was generated with a −20% systematic error in $\bar{f}_B$ and a −10% error in $\bar{f}_A$ and no random errors. FIG. 9 was generated under the same conditions, but with an additional random noise component of ±5% in both mean frequency values. FIG. 10 shows the resulting displayed vector field for flow now at 90° to the transducer face under the same conditions as FIG. 9. In each case the errors in the magnitude increase with depth indicated by the larger localized vectors and the colors. The errors in vector direction appear to be fairly constant throughout all three images though the direction around y =40 mm down to a depth around 60 mm appear to be less accurate. In contrast to the control FIGS. 6 and 7, the 2-D maps, despite significant introduced errors, still manage to convey the true nature of the flow field.

Experimental Verification of Concept

The efficacy of the invention was proven by undertaking a representative 2D in-vitro experiment to show that the novel apparatus and method are capable of accurately detecting 2-D motion at arbitrary angles. An experimental scanner at Duke University Medical Center in Durham, N.C. was used in conjunction with a linear array of 64 elements (piezoelectric crystals) to measure the magnitude and direction of translation for a phantom blood target. Assuming that the transmitted pulses were equally spaced in time at the Doppler pulse repetition interval, a magnitude of translation can be related to a target velocity.

The array aperture of 40.95 mm was logically divided into two adjacent equally sized sub-apertures. The center frequency used was 2.0 MHz with an approximate FWHM (full width half maximum) −3 dB bandwidth of 40%. The transmit and receive foci were fixed at 37 mm in the transmit direction from sub-aperture B. This location was chosen to be within ±30° of each element in the array so as to reduce possible deleterious effects due to poor angular responses at larger angles. The phantom target consisted of graphite powder in agar spheres in a propanol/water mixture.

The RF speckle patterns from this target, received by each sub-aperture after insonification by one sub-aperture, were digitized at 50 MHz after each of 32 target translations by a fixed magnitude and direction. These data were then processed off-line by using the Hilbert transform quadrature detection technique described hereinbelow. A single point from each filtered waveform was taken at a fixed time delay, corresponding to the selected focus, forming a 32-point ensemble. This was then processed by the standard autocorrelation mean frequency estimator, from which the corresponding translation was calculated.

Translations were made with five different magnitudes, spanning the aliasing limit, in each of three directions ($\theta_v$=0°, 45°, and 79° away from the transducer face) using a manual 3-axis translation stage. This entire procedure of 15 sets of translations was completed six times, each time with a new speckle pattern formed by thoroughly mixing the sub-resolution scatterers within the phantom mixture.

Figure 11:
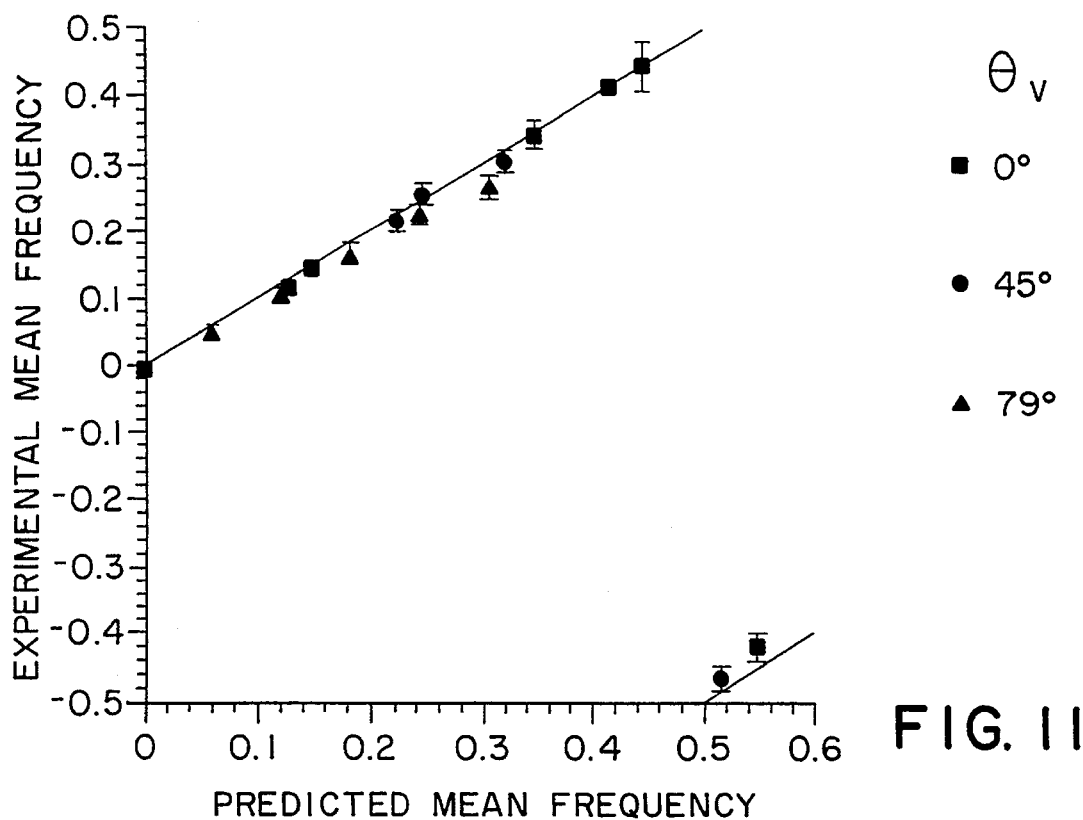
FIG. 11 shows an experimental versus predicted mean frequency from the back-scatter sub-aperture B using a 40.95 mm phased array transducer on the scanner and conventional autocorrelation mean frequency processing wherein error bars indicate one standard deviation from six sets of each of 32 ensembles.
Figure 12:
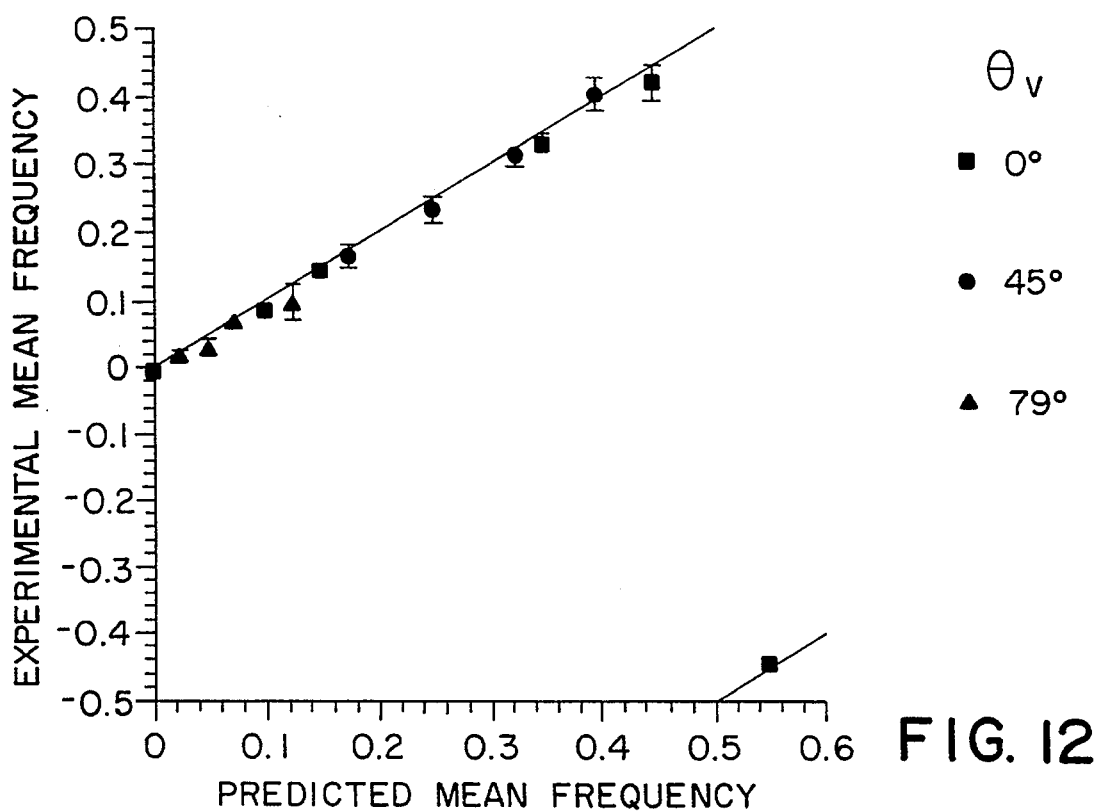
FIG. 12 shows an experimental versus predicted mean frequency from the angular sub-aperture A using a 40.95 mm phased array transducer and conventional autocorrelation mean frequency processing wherein error bars indicate one standard deviation from six sets of each of 32 ensembles.
Figure 13:
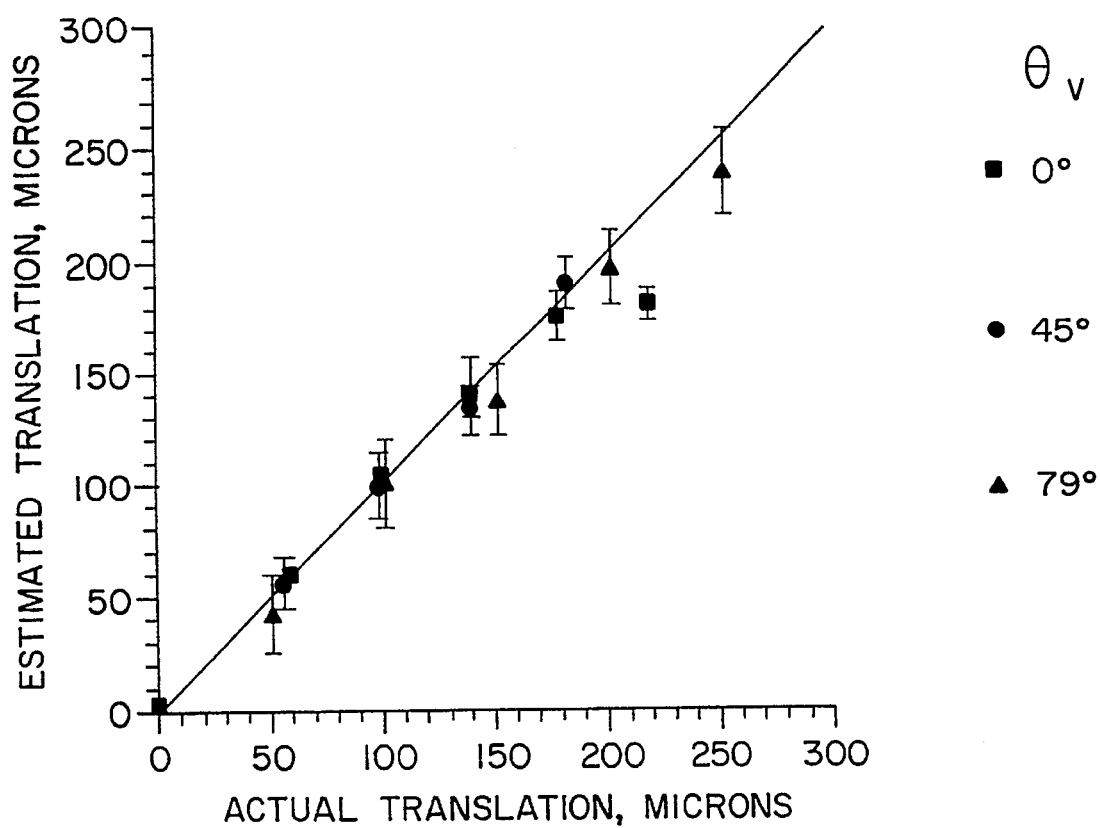
FIG. 13 shows an estimated versus actual translation for three different angles of motion relative to the transducer geometry as shown in FIG. 2 using the new vector velocity mapping technique and data plotted in FIGS. 11 and 12.
Figure 14:
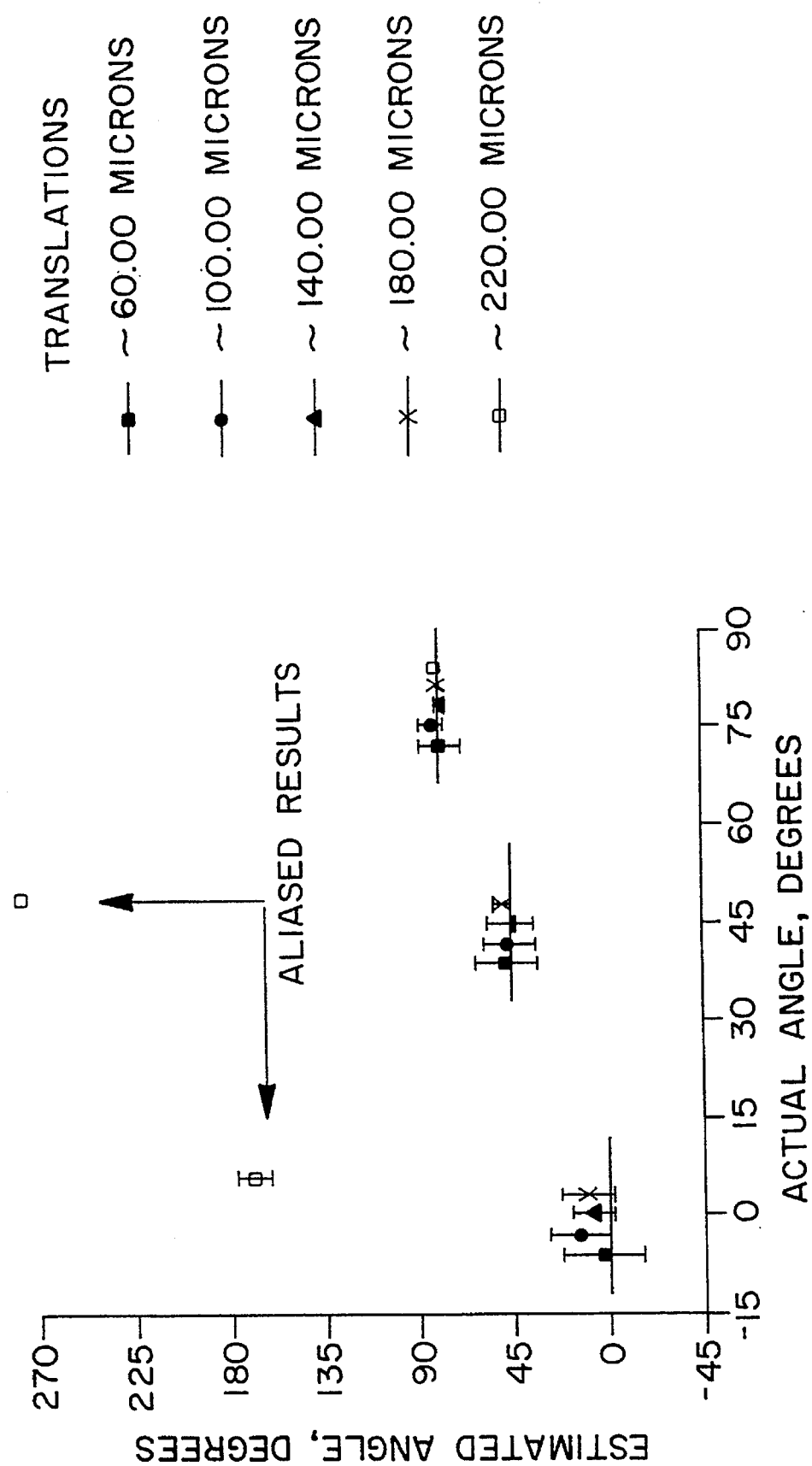
FIG. 14 shows an estimated versus actual direction of translation for five different translation magnitudes using the new vector velocity mapping technique and data plotted in FIGS. 11 and 12 wherein for clarity, a small horizontal offset has been added to some of the data sets grouped around the three translation directions and wherein in each group, the ideal case is indicated by the short horizontal line.

Experimental results are shown in FIGS. 11 through 14. FIGS. 11 and 12 show a close correlation between the predicted and experimental mean frequencies (normalized to the PRF) for each of the translations. FIGS. 13 and 14 show the result of using these mean frequency estimates in calculating the 2-D velocity (vectorial translation) and angle as compared to the known velocity and angle. Where the data are not aliased, experimental results closely match the actual translations, demonstrating the viability of the inventive technique of the present invention.

Figure 15:
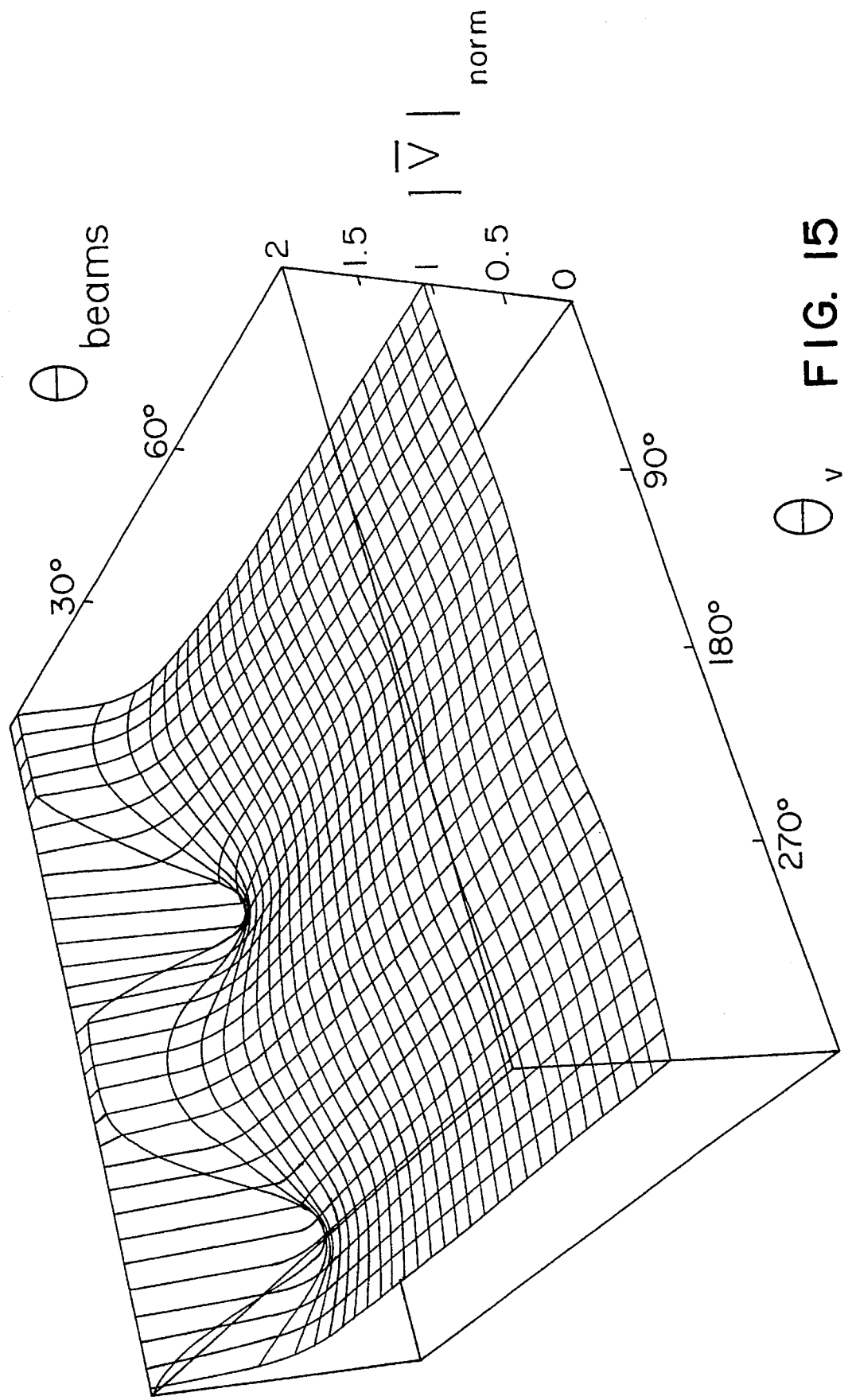
FIG. 15 shows a plot of normalized estimated vector velocity magnitude versus flow direction and angle between back-scatter and angular-scatter beams wherein a 5% error in the back-scatter mean frequency has been added showing degradation in performance as the angle between the receive beams approaches zero.

The simulations presented above show that errors introduced into the mean frequency estimates for each sub-aperture result in a spatially inhomogeneity in the calculated quantities within the scan plane for a homogeneous flow field. This variation is due predominantly to the reduction in the angle between the beams for increasing range. This is to be expected since in the limiting case where the angle between the beams is zero, the system is reduced to a conventional 1-D Doppler system. This is shown in the graph of FIG. 15 which plots the normalized estimated velocity magnitude as a function of the flow direction ($\theta_v$) and the angle between the beams ($\theta$beams) for a 5% systematic error in $\bar{f}_B$ and no error in $\bar{f}_A$. It can be seen that, as the angle between the beams, $\theta$beams, approaches zero, the system has the normal sinusoidal variation with angle as in a conventional 1-D system. FIG. 15 also shows the reduced error for shallower scans.

Figure 16:
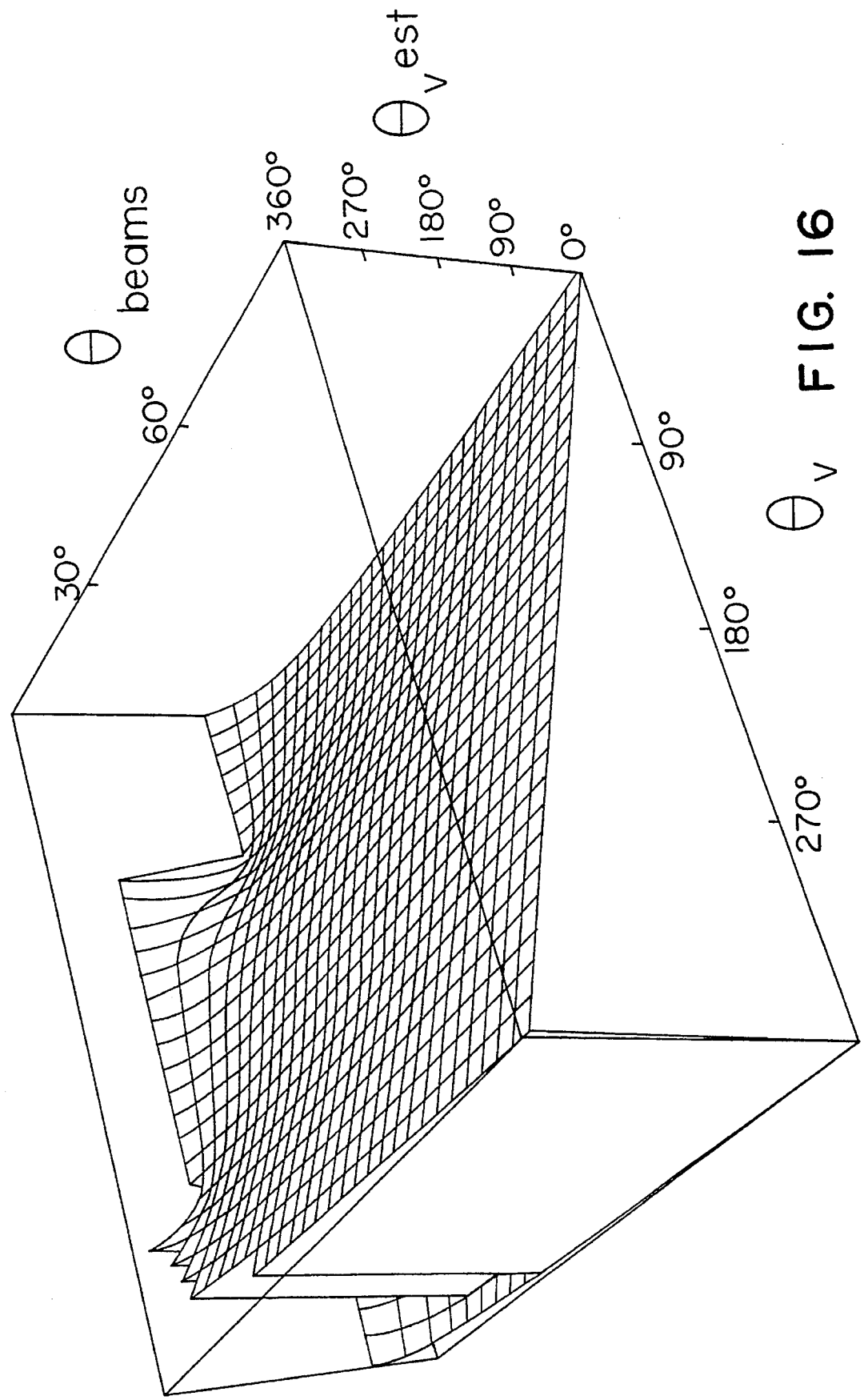
FIG. 16 shows a plot of estimated vector direction versus flow direction and angle between back-scatter and angular-scatter beams wherein a 5% error was added to the back-scatter mean frequency estimate showing degradation in performances as the angle between the beams approaches zero and wherein the discontinuity in the top left-hand corner of the graph is a wrapping around from 360° to 0°.

A plot of the estimated angle shows similar characteristics (FIG. 16), with the largest error occurring when the flow direction is near 0° or 180 ° (i.e., purely "axial" flow) and the angle between receive beams is small. This is due to the arctangent function having the maximum rate of change in this vicinity. It should be observed that the apparent large error in the top left-hand corner is simply a wrapping around from 360° back to zero.

The best performance is attained when the angle between the beams is large so that one is measuring as much of the orthogonal components of the flow as possible.

The magnitude of error in the mean frequency estimates will obviously determine the overall accuracy of the technique in measuring 2-D velocity fields, but it is the difference in errors between each sub-aperture that most strongly affects the accuracy in the final calculated field. This arises because of the ratio of the two mean frequencies in Eq. (5). If the degree of error in $\bar{f}_A$ and $\bar{f}_B$ were approximately equal in the simulations, near perfect results for the estimated angle and a uniform error in magnitude across the scan plane would be observed. This was confirmed with additional simulations. A number of plots similar to those shown in FIGS. 3 and 4 for many different directions revealed that the maximum error down to a depth of ~100 mm for a 1% error in either $\bar{f}_A$ or $\bar{f}_B$ was ~5% for the magnitude and ~5° for the angle.

The experimental study showed the viability of the inventive angular-scatter, beam-tracking technique in measuring velocity vectors in two dimensions. From the calculated mean frequencies, both the velocity magnitude and direction were accurately detected. The rms error in the mean frequencies determined from the in vitro experiment was ~10% for the angular-scattered sub-aperture A, and about half that for the back-scattered sub-aperture B (these rms errors did not include aliased values). Variations around these mean values are primarily a result of speckle and inaccuracies in the manual translation system. The rms error was less than 5% in the velocity magnitude and a little over 4° in the angle, excluding aliased values once again. These results confirm the theory and simulations described earlier. Applicants note from the error bars that angle estimation is better for angles closer to 90° than for angles close to zero which is primarily a result of the arctangent phenomenon described earlier.

The aliased results clearly seen in FIG. 14 help point out the difference between applicants' new apparatus and a conventional 1-D apparatus. If the mean frequency estimates from both sub-apertures are aliased, the magnitude is underestimated and the direction reversed. When only one mean frequency is aliased then both the direction and magnitude are grossly inaccurate. This latter phenomenon occurred for a 226 μm translation of 45° where the estimated angle was calculated to be 82.2°. In such a case, this result may be difficult to distinguish from a severely disturbed flow pattern.

Conclusions Re Experimental Verification

Applicants' novel ultrasound phased array transducer configuration introduces a new ultrasound imaging technique for detecting multi-dimensional velocity vectors using a conventional phased array transducer. By electronically separating the phased array into independently controlled sub-apertures, a transmitted pulse can be tracked from different angles simultaneously, allowing true velocity vectors to be measured over a significant field of view in real time. Applicants' invention provides more accurate information to the clinician regarding the behavior of blood flow than is possible with present color flow mapping systems.

Applicants have demonstrated above that the most accurate results are achieved when the angle between beam axes is large, and that the performance degrades with scan depth. This depth-dependent degradation is because the angles become smaller with increasing depth when conventional phased arrays are used. Despite this limitation with conventional phased arrays, simulations of typical errors and in vitro experiments have shown that the system is still able to convey information about the nature of blood flow without the use of specialized transducers and without compromise to the frame rate. The only requirements are a modest increase in computer-processing capability (relative to that required for conventional 1-D systems) and a flexible beamformer. More specialized phased arrays can be utilized to improve the angle between received directions, and these specialized phased arrays will be described in more detail hereinbelow.

Practical Description of the Invention

Applicants' novel ultrasound apparatus and method comprises electronically and/or mechanically dividing a phased array transducer into two or more independently controlled groups of elements (sub-apertures) and transmitting from a group of elements at the end or a group formed from less than the full amount of elements in the phased array and simultaneously receiving with two or more groups (see FIGS. 19A–19E). The coherent transmit pulse(s) must be from a favorable angle(s). By utilizing these subgroups within a phased array (or more specifically sub-apertures) the detectable lateral component of any movement/flow is greater assuming the phased array transducer is properly oriented and the appropriate sub-apertures are used. By being able to detect more of the lateral components using applicants' novel technique, compared to a conventional scanner or a 2-D technique that transmits with the full array or perpendicular to the face of a phased array, more accurate vector estimates are possible.

The best one could do prior to applicants' invention would be to transmit/receive (TX/RX) with two orthogonally positioned transducers but this transducer arrangement is not clinically acceptable and is difficult to implement from a practical standpoint. Therefore, conventional phased array transducers are used but the majority of the practical scanning directions limits the amount of the lateral component of any movement that can be measured. Thus, there is a long-felt need for an improved ultrasound imaging apparatus and method which can better measure the lateral component of blood flow in a subject being analyzed.

Using a conventional phased array, currently available systems are more sensitive and more accurate at detecting axial flow than lateral flow. Therefore, if one uses 2 or more beams to measure the 2 orthogonal components (or 3 orthogonal components for the 3D case) and you consider noise in the system, one wants to measure as much of the lateral component as possible. By offsetting and reducing the size of the transmit and/or receive sub-apertures applicants have accomplished this. Various combinations of transmit and/or receive sub-aperture configurations are shown in FIGS. 19A–19E and FIGS. 20A–20D, but these illustrations are not intended to depict all embodiments of the novel phased array transducer configurations contemplated by applicants' invention.

Several conventional and more specialized phased array transducers with possible realizations of different sub-aperture configurations for measuring two-dimensional (2D) and three-dimensional (3D) motion/blood flow are shown in FIGS. 19A–19E and FIGS. 20A–20D, respectively. These planar and non-planar phased array transducers can contain a single mechanical section or a plurality of mechanical sections within a 1D linear array of piezoelectric elements or a 2D grid of piezoelectric elements. Each mechanical section can be electronically addressed as one or more sub-apertures similar to the configurations described in FIGS. 19A–19E. It is also contemplated that a 1D linear array of piezoelectric elements can be mechanically configured into a concave phased array transducer (see FIG. 20D) and electronically addressed, again, similar to the FIGS. 19A–19E.

Because of the possible asymmetry that exists with this type of approach, the relationship between the received signals and the scanned space/tissue can be non-linear for any receive sub-aperture with its center not coincident with the center of the transmit sub-aperture.

If this relationship is not considered and properly handled the final real-time displayed velocity map could be inaccurate and/or misregistered. This nonlinearity does not present a serious problem and therefore a source of serious inaccuracies for small inter-beam angles, but the purpose of applicants' invention is to increase the inter-beam angles to improve the accuracy of velocity detection and present a 2-D (or 3-D) vector velocity mapping apparatus and method.

For relatively large inter-beam angles which most often occur close to a conventional transducer, it is necessary to decimate and/or average the received data stream in this non-linear fashion. This can be done using dedicated look-up tables (LUT) or programmed microprocessors, for example. In one implementation a microprocessor can be programmed to do the non-linear signal detection/extraction and also perform the necessary clutter filtering for the removal of non-flow or undesired signals. Depending upon the site of the desired color map, it may be necessary to use more than one microprocessor of the type that is currently available today (such as the TEXAS INSTRUMENTS Model No. TMS320C30 digital signal microprocessor).

Novel Quadrature Circuitry

Optionally, applicants' contemplate further image enhancement in terms of accuracy as also available by utilizing a novel and more accurate quadrature detection circuit. Generally, by implementing a quadrature detection scheme based on the well-known Hilbert transform, more accurate quadrature signals can be made available to the vector velocity mapping system contributing to the over-all ultrasonic system accuracy.

Figure 17:
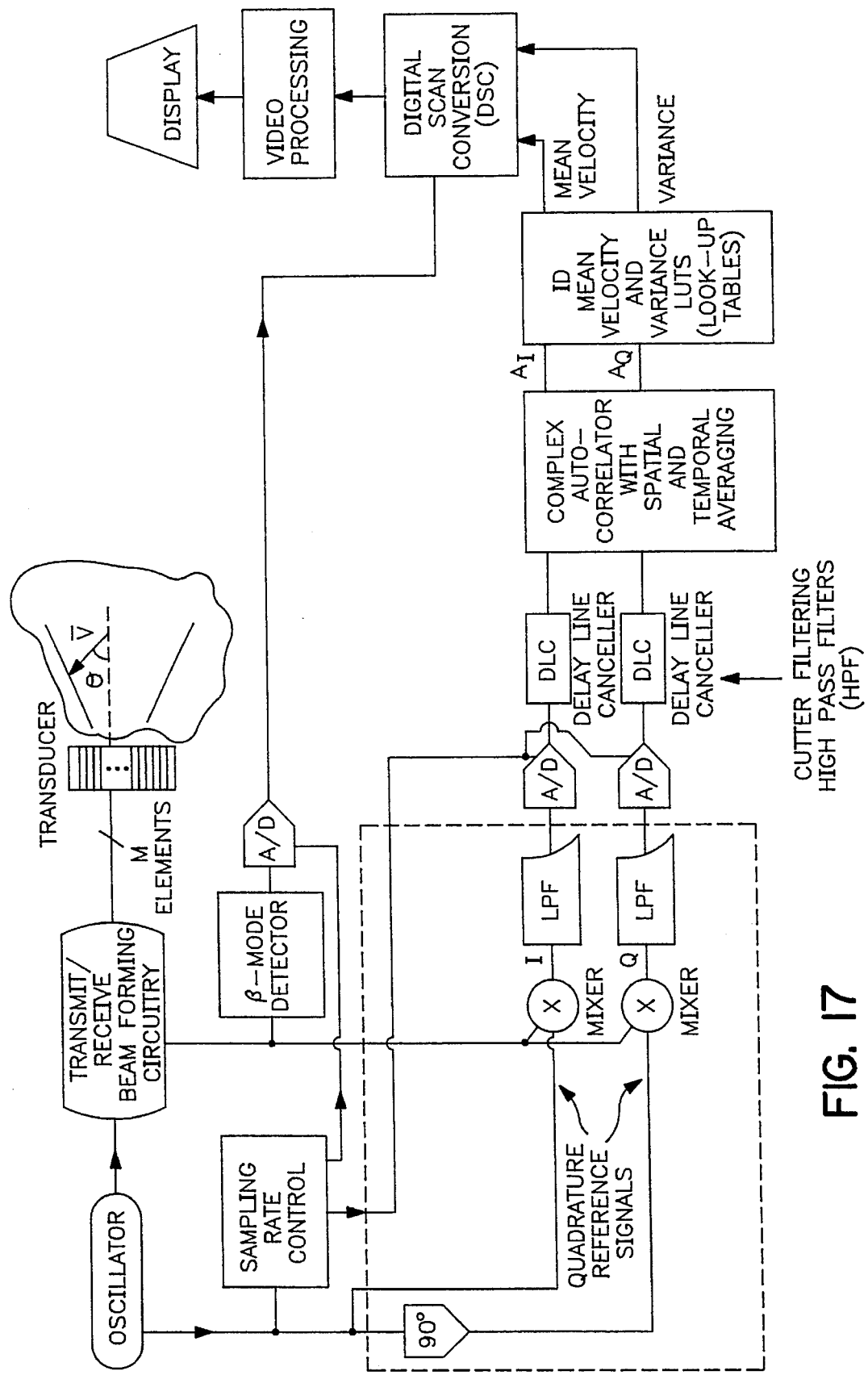
FIG. 17 is a simplified schematic diagram of a conventional ultrasonic scanner using quadrature reference signal circuitry.
Figure 18:
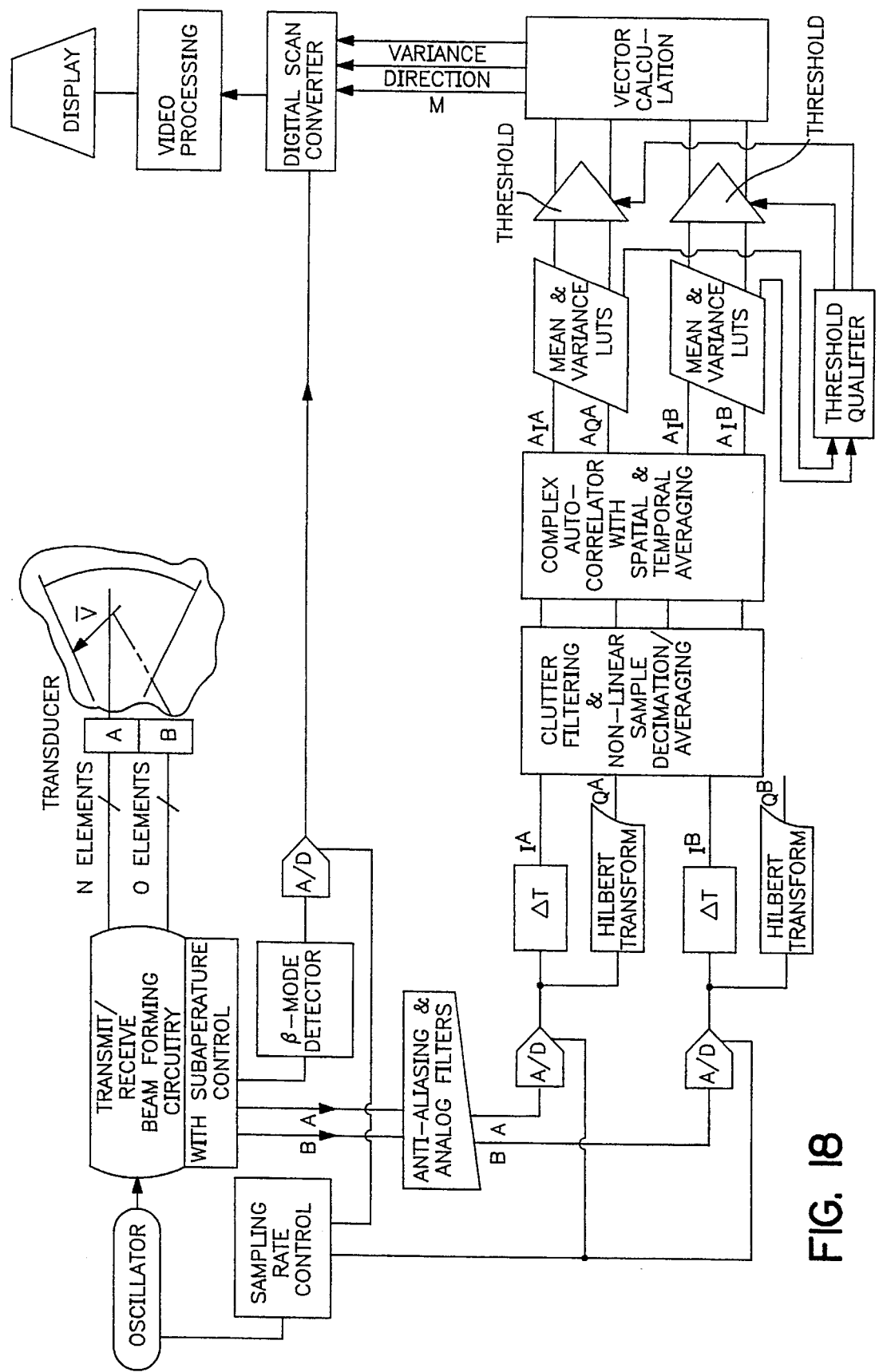
FIG. 18 is a schematic diagram of the ultrasonic scanner apparatus of the invention utilizing the novel phased array transducer configuration and the novel quadrature reference signal circuitry as described herein.
Figure 19A:
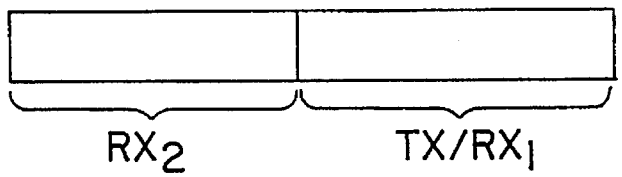
FIGS. 19A–19E is a schematic drawing of several possible phased array transducer configurations according to the present invention for transmitting pulses and receiving reflected echoes.
Figure 19B:
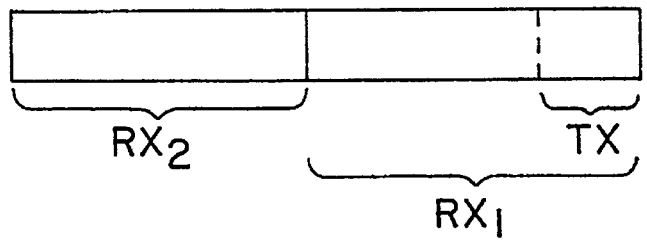
Figure 19C:
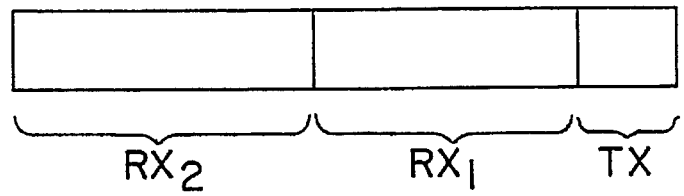
Figure 19D:
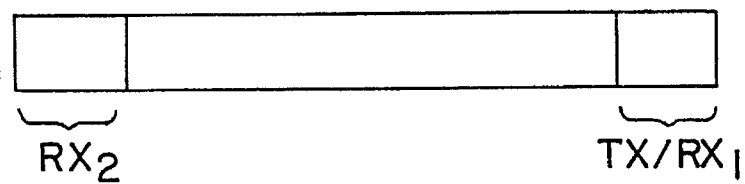
Figure 19E:
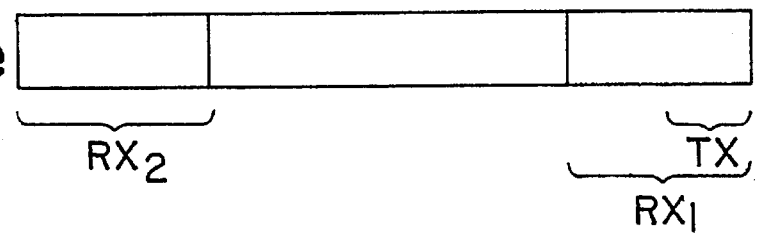

Since high-speed digital signal processing (DSP) hardware and analog-to-digital (A/D) converters are now readily available, an implementation can be realized that does not demand a conventional demodulation scheme and its associated hardware as shown in the simplified schematic of a conventional ultrasound imaging apparatus depicted in FIG. 17. Applicants contemplate sampling the filtered analog received RF signals or a downshifted version of these signals at sufficient speed and digitally filtering these signals with a Hilbert transform impulse response (see FIG. 18) so as to eliminate the mixers, low-pass filters (LPF), and quadrature reference frequencies associated with prior art demodulation schemes (see FIG. 17). In addition to the elimination of these components, the often difficult task of matching the amplitude and phase of the two I and Q (In-phase and Quadrature) channels is eliminated. This novel approach also provides true quadrature signals where each frequency within the filtered signal has been shifted by the appropriate 90 degrees unlike traditional demodulation schemes wherein only the frequency used for mixing is truly shifted by 90 degrees. As the currently available systems move towards larger bandwidths this scheme will be even more attractive. As can be seen in FIG. 18, the novel quadrature circuit of the invention is provided for each of the circuits associated, respectively, with sub-aperture A and sub-aperture B.

The ultrasound imaging circuits shown in FIGS. 17 and 18 will not be discussed in further detail herein since applicants believe that one of ordinary skill in the ultrasound imaging art will be familiar with the conventional circuitry of FIG. 17 and understand the inventive modifications to the transducers and quadrature circuitry thereof as shown in FIG. 18.

It will be understood that various details of the invention may be changed without departing from the scope of the invention. Furthermore, the foregoing description is for the purpose of illustration only, and not for the purpose of limitation—the invention being defined by the claims.

What is claimed is:

1. In an improved ultrasonic blood flow imaging apparatus comprising ultrasonic transducer means adapted to repeatedly transmit ultrasonic pulse beams into a subject under examination and to receive reflected echoes of the ultrasonic pulse beams from within the subject and convert the reflected echoes into echo signals, signal processing means for converting said reflected echo signals via Doppler signal processing into image signals, and display means for visually outputting said image signals as an image, the improvement comprising:

(a) ultrasonic transducer means comprising a phased array transducer divided into two or more independently controlled sub-apertures and adapted for transmitting ultrasonic pulse beams from at least one of said two or more sub-apertures and for receiving the reflected echoes with at least two of said two or more sub-apertures, such that at least one sub-aperture is receiving an echo from a pulse beam that the at least one sub-aperture did not transmit;

whereby real time multi-dimensional blood flow imaging with enhanced sensitivity to lateral blood flow is achieved.

2. An ultrasonic blood flow imaging apparatus according to claim 1 wherein said phased array transducer is electronically divided into two sub-apertures and adapted for transmitting from one of said two sub-apertures and for receiving with both of said two sub-apertures.

3. An ultrasonic blood flow imaging apparatus according to claim 1 wherein said phased array transducer is electronically divided into three sub-apertures and adapted for transmitting from one sub-aperture and for receiving with two sub-apertures.

4. An ultrasonic blood flow imaging apparatus according to claim 1 wherein said phased array transducer is physically divided into two planar sub-apertures which define a non-planar phased array transducer, and adapted for transmitting from one of said two sub-apertures and for receiving with both of said two sub-apertures.

5. An ultrasonic blood flow imaging apparatus according to claim 1 wherein said phased array transducer is physically divided into a plurality of two dimensional planar sub-apertures which define a three dimensional non-planar phased array transducer, and adapted for transmitting from one or more of said plurality of sub-apertures and for receiving with two or more of said plurality of sub-apertures.

6. An ultrasonic blood flow imaging apparatus according to claim 1 wherein said phased array transducer is physically divided into two or more sub-apertures defining a non-planar phased array transducer comprising a plurality of sections, and wherein each of said sections is electronically addressed as two or more sub-apertures.

7. An ultrasonic blood flow imaging apparatus according to claim 1 wherein said phased array transducer comprises a plurality of piezoelectric crystals electronically divided into two or more sub-apertures.

8. The apparatus of claim 1, wherein the at least one sub-aperture receives by tracking the pulse beam that the at least one sub-aperture did not transmit.

9. An improved ultrasonic blood flow imaging apparatus comprising ultrasonic transducer means adapted to repeatedly transmit ultrasonic pulse beams into a subject under examination and to receive reflected echoes of the ultrasonic pulse beams from within the subject and convert the reflected echoes into echo signals, signal processing means for converting said reflected echo signals via Doppler signal processing into image signals, and display means for visually outputting said image signals as an image, the improvement comprising:

(a) ultrasonic transducer means comprising a phased array transducer divided into two or more independently controlled sub-apertures and adapted for transmitting ultrasonic pulse beams from at least one of said two or more sub-apertures and for receiving the reflected echoes with at least two of said two or more sub-apertures, such that at least one sub-aperture is receiving an echo from a pulse beam that the at least one sub-aperture did not transmit; and (b) signal processing means including quadrature detection circuitry comprising sampling means for sampling said echo signals or a downward shifted version of said echo signals and Hilbert transform means for filtering said signals;

whereby real time multi-dimensional blood flow imaging with enhanced sensitivity to lateral flow is achieved.

10. An ultrasonic blood flow imaging apparatus according to claim 9 wherein said phased array transducer is electronically divided into two sub-apertures and adapted for transmitting from one of said two sub-apertures and for receiving with both of said two sub-apertures.

11. An ultrasonic blood flow imaging apparatus according to claim 9 wherein said phased array transducer is electronically divided into three sub-apertures and adapted for transmitting from one sub-aperture and for receiving with two sub-apertures.

12. A method according to claim 9 comprising physically dividing said phased array transducer into two planar sub-apertures which define a non-planar phased array transducer and transmitting from one of said two sub-apertures and receiving with both of said sub-apertures.

13. A method according to claim 9 comprising physically dividing said phased array transducer into a plurality of two dimensional planar sub-apertures which define a three dimensional non-planar phased array transducer and transmitting from one or more of said plurality of sub-apertures and receiving with two or more of said plurality of sub-apertures.

14. A method according to claim 9 comprising physically dividing said phased array transducer into two or more sub-apertures defining a non-planar phased array transducer comprising a plurality of sections, and electronically addressing each of said sections as two or more sub-apertures.

15. An ultrasonic blood flow imaging apparatus according to claim 9 wherein said linear array transducer comprises a plurality of piezoelectric crystals electronically divided into two or more sub-apertures.

16. The apparatus of claim 9, wherein the at least one sub-aperture receives by tracking the pulse beam that the at least one sub-aperture did not transmit.

17. In a method for improved ultrasonic blood flow imaging comprising utilizing a phased array transducer for repeatedly transmitting ultrasonic pulse beams into a subject under examination, receiving reflected echoes of the ultrasonic pulse beams from within the subject and converting the reflected echoes into echo signals; utilizing signal processing means for converting said reflected echo signals via Doppler signal processing into image signals; and utilizing display means for visually outputting said image signals as an image, the improvement comprising:

(a) electronically dividing said phased array transducer into two or more independently controlled sub-apertures; and (b) transmitting ultrasonic pulse beams from at least one of said two or more sub-apertures and receiving the reflected echoes with at least two of said two or more sub-apertures, such that at least one sub-aperture is receiving an echo from a pulse beam that the at least one sub-aperture did not transmit;

whereby real time multi-dimensional blood flow imaging with enhanced sensitivity to lateral blood flow is achieved.

18. A method according to claim 17 comprising dividing said phased array transducer into two sub-apertures and transmitting from one of said two sub-apertures and receiving with both of said sub-apertures.

19. A method according to claim 17 comprising dividing said phased array transducer into three sub-apertures and transmitting from one sub-aperture and receiving with two sub-apertures.

20. A method according to claim 17 comprising physically dividing said phased array transducer into two planar sub-apertures which define a non-planar phased array transducer and transmitting from one of said two sub-apertures and receiving with both of said sub-apertures.

21. A method according to claim 17 comprising physically dividing said phased array transducer into a plurality of two dimensional planar sub-apertures which define a three dimensional non-planar phased array transducer and transmitting from one or more of said plurality of sub-apertures and receiving with two or more of said plurality of sub-apertures.

22. A method according to claim 17 comprising physically dividing said phased array transducer into two or more sub-apertures defining a non-planar phased array transducer comprising a plurality of sections, and electronically addressing each of said sections as two or more sub-apertures.

23. The method of claim 17, wherein the at least one sub-aperture receives by tracking the pulse beam that the at least one sub-aperture did not transmit.

24. In a method for improved ultrasonic blood flow imaging comprising utilizing a phased array transducer for repeatedly transmitting ultrasonic pulse beams into a subject under examination, receiving reflected echoes of the ultrasonic pulse beams from within the subject and converting the reflected echoes into echo signals; utilizing signal processing means for converting said reflected echo signals via Doppler signal processing into image signals; and utilizing display means for visually outputting said image signals as an image, the improvement comprising:

(a) electronically dividing said phased array transducer into two or more independently controlled sub-apertures;

(b) transmitting ultrasonic pulse beams from at least one of said two or more sub-apertures and receiving the reflected echoes with at least two of said two or more sub-apertures, such that at least one sub-aperture is receiving an echo from a pulse beam that the at least one sub-aperture did not transmit; and (c) providing quadrature detection circuitry within said signal processing means for sampling said echo signals or a downward shifted version of said echo signals and filtering the samples of said signals with Hilbert transformations;

whereby real time multi-dimensional blood flow imaging with enhanced sensitivity to lateral blood flow is achieved.

25. A method according to claim 24 comprising dividing said phased array transducer into two sub-apertures and transmitting from one of said two sub-apertures and receiving with both of said sub-apertures.

26. A method according to claim 24 comprising dividing said phased array transducer into three sub-apertures and transmitting from one sub-aperture on one end of the linear array transducer and receiving with the remaining two sub-apertures.

27. A method according to claim 24 comprising physically dividing said phased array transducer into two planar sub-apertures which define a non-planar phased array transducer and transmitting from one of said two sub-apertures and receiving with both of said sub-apertures.

28. A method according to claim 24 comprising physically dividing said phased array transducer into a plurality of two dimensional planar sub-apertures which define a three dimensional non-planar phased array transducer and transmitting from one or more of said plurality of sub-apertures and receiving with two or more of said plurality of sub-apertures.

29. A method according to claim 24 comprising physically dividing said phased array transducer into two or more sub-apertures defining a non-planar phased array transducer comprising a plurality of sections, and electronically addressing each of said sections as two or more sub-apertures.

30. The method of claim 24, wherein the at least one sub-aperture receives by tracking the pulse beam that the at least one sub-aperture did not transmit.

* * * * *

UNITED STATES PATENT AND TRADEMARK OFFICE
CERTIFICATE OF CORRECTION

PATENT NO. : 5,522,393
DATED : June 4, 1996
INVENTOR(S) : Patrick J. Phillips and Olaf T. von Ramm It is certified that error appears in the above-indentified patent and that said Letters Patent is hereby corrected as shown below:

Drawings:

Figure 18, continue the line coming from the right side of the block labelled "HILBERT TRANSFORM" so that the line connects to the next block labelled "CLUTTER FILTERING & NON-LINEAR SAMPLE DECIMATION/AVERAGING.

Column 2, line 9, after "space;" and in front of "(5)", begin a new line.

Column 4, line 47, change "performances" to read as -- performance --.

Signed and Sealed this

Twenty-sixth Day of November 1996

Attest:

BRUCE LEHMAN

Attesting Officer

Commissioner of Patents and Trademarks